United States Patent
Willcut et al.

(10) Patent No.: US 10,507,337 B2
(45) Date of Patent: Dec. 17, 2019

(54) RADIOTHERAPY TREATMENT PLAN OPTIMIZATION WORKFLOW

(71) Applicant: Elekta, Inc., Atlanta, GA (US)

(72) Inventors: Virgil Matthew Willcut, Atlanta, GA (US); Spencer Marshall, Atlanta, GA (US)

(73) Assignee: Elekta, Inc., Atlanta, GA (US)

( * ) Notice: Subject to any disclaimer, the term of this patent is extended or adjusted under 35 U.S.C. 154(b) by 272 days.

(21) Appl. No.: 15/702,981

(22) Filed: Sep. 13, 2017

(65) Prior Publication Data

US 2019/0076671 A1 Mar. 14, 2019

(51) Int. Cl.
*A61N 5/10* (2006.01)

(52) U.S. Cl.
CPC ......... *A61N 5/1031* (2013.01); *A61N 5/1037* (2013.01); *A61N 5/1038* (2013.01);
(Continued)

(58) Field of Classification Search
CPC .. A61N 5/1031; A61N 5/1038; A61N 5/1045; A61N 5/1037; A61N 5/1039;
(Continued)

(56) References Cited

U.S. PATENT DOCUMENTS

| 9,764,162 | B1 * | 9/2017 | Willcut | G16H 50/30 |
| 2005/0207531 | A1 * | 9/2005 | Dempsey | A61N 5/1031 378/65 |

(Continued)

FOREIGN PATENT DOCUMENTS

| EP | 2574374 | 4/2013 |
| WO | 2016023786 | 2/2016 |

(Continued)

OTHER PUBLICATIONS

"International Application Serial No. PCT US2018 050628, International Search Report dated Jan. 7, 2019", 5 pgs.

(Continued)

*Primary Examiner* — Michael C Bryant
(74) *Attorney, Agent, or Firm* — Schwegman Lundberg & Woessner, P.A.; Sanjay Agrawal

(57) ABSTRACT

Systems and methods for performing radiation treatment planning are provided. An exemplary system may include a processor device communicatively coupled to a memory device and configured to perform operations when executing instruction stored in the memory device. The operations may include receiving a reference treatment plan including one or more dose constraints and determining, based on the reference treatment plan, segment information of a plurality of radiation beams. The operations may also include determining a fluence map for each of the plurality of radiation beams based on the one or more dose constraints using a fluence map optimization algorithm. The operations may also include determining a dose distribution based on the fluence maps of the plurality of radiation beams. The operations may also include determining at least one beam modulation property of a new treatment plan using a warm-start optimization algorithm based on the segment information and the dose distribution.

28 Claims, 15 Drawing Sheets

(52) U.S. Cl.
CPC ......... *A61N 5/1039* (2013.01); *A61N 5/1045* (2013.01); *A61N 5/1049* (2013.01); *A61N 5/1064* (2013.01); *A61N 5/1071* (2013.01); *A61N 5/1077* (2013.01); *A61N 2005/1041* (2013.01)

(58) Field of Classification Search
CPC .......... A61N 2005/1041; A61N 5/1071; A61N 5/1049; A61N 5/1064; A61N 5/1077
See application file for complete search history.

(56) References Cited

U.S. PATENT DOCUMENTS

| | | | | |
|---|---|---|---|---|
| 2012/0123184 | A1* | 5/2012 | Otto | A61N 5/1067 600/1 |
| 2012/0323599 | A1* | 12/2012 | Bal | A61N 5/1031 705/2 |
| 2016/0303398 | A1* | 10/2016 | Eriksson | A61N 5/1031 |
| 2018/0193674 | A1* | 7/2018 | Brooks | A61N 5/1049 |

FOREIGN PATENT DOCUMENTS

| | | |
|---|---|---|
| WO | 2017118725 | 7/2017 |
| WO | 2019055491 | 3/2019 |

OTHER PUBLICATIONS

"International Application Serial No. PCT US2018 050628, Written Opinion dated Jan. 7, 2019", 6 pgs.

Ahunbay, Ergun E, "An online replanning method using warm start optimization and aperture morphing for flattening-filter-free beams", Medical Physics, [Online] Retrieved from the internet:https:s3.amazonaws.com objects.readcube.com articles downloaded wiley 6e57bc2941e4c45ebccde6e4bb426ablad98aa9c500b252b877bcb38 4feb70b4.pdf?X, (Aug. 1, 2016), 4575-4584 pgs.

* cited by examiner

RADIOTHERAPY TREATMENT PLAN OPTIMIZATION WORKFLOW

TECHNICAL FIELD

This disclosure relates generally to radiation therapy or radiotherapy. More specifically, this disclosure relates to systems and methods for optimizing radiotherapy treatment plans.

BACKGROUND

Radiotherapy is used to treat cancers and other ailments in mammalian (e.g., human and animal) tissue. An exemplary radiotherapy is provided using a linear accelerator (LINAC), whereby a target (e.g., a tumor) is irradiated by high-energy particles (e.g., electrons, photons, ions and the like). In a typical LINAC-based radiation treatment, multiple radiation beams are directed towards the target from different angles.

The surrounding normal tissue is often called an organ at risk (OAR). To prevent OARs from the severe collateral damage caused by the radiation beams, the doses received by these OARs should be limited to a certain level. Such limitations on the doses received by the OARs, often called constraints, need to be satisfied during treatment planning.

Treatment planning is a process involving determination of specific radiotherapy parameters (e.g., radiation beam angles, radiation intensity level at each angle, etc.) for implementing a treatment goal under the constraints. The outcome of the treatment planning exercise is a radiotherapy treatment plan, hereinafter also referred to as a treatment plan or simply a plan. A typical treatment planning process includes delineating one or more targets and one or more OARs from a medical image of the patient, specifying radiation beam angles, or a range of angles in the case of an arc plan, and determining an aperture shape or shapes and radiation intensity levels for each shape at each beam angle. The combination of shape, intensity, collimator angle, and jaw settings at each gantry angle is called a control point and it this information that is transferred to the delivery device to dictate the machine delivery. Optimization is usually carried out with respect to one or more plan parameters to reduce beam-on time, improve dose uniformity, etc.

Creation of a treatment plan can be a time-consuming process where a planner tries to comply with various treatment objectives or constraints, considering their individual importance to produce a treatment plan which is clinically acceptable. Therefore, it is desirable to reduce the planning time with an improved radiotherapy treatment planning workflow.

SUMMARY

Certain embodiments of the present disclosure relate to a radiotherapy treatment planning system. The system may include a memory device storing computer-executable instructions. The system may also include at least one processor device communicatively coupled to the memory device. The computer-executable instructions, when executed by the at least one processor device, may cause the processor device to perform various operations for radiotherapy treatment planning. The operations may include receiving a reference treatment plan. The reference treatment plan can include one or more dose constraints for targets and/or OARs and control point information. The operations may also include receiving at least one medical image and a structure set not included with the received reference treatment plan. The operations may also include determining a new treatment plan based on the received at least one medical image and structure set. The operations may also include determining, such as based on the reference treatment plan, control point information of a plurality of radiation beams and registering the plurality of radiation beams to the received at least one medical image. The operations may also include determining an optimized fluence map for each of the plurality of radiation beams, such as based on the one or more dose constraints included in the reference treatment plan, such as by using a fluence map optimization algorithm and the received at least one medical image and structure set. The operations may also include determining an optimized dose distribution, such as based on the optimized fluence maps for the plurality of radiation beams. The operations may also include determining at least one beam modulation property of the new treatment plan, such as by using a warm-start optimization algorithm, such as can be based on the control point information included in the reference treatment plan by optimizing shapes and/or weights of the control points and/or weights of the plurality of radiation beams, such as to achieve the optimized dose distribution. The new treatment plan can be for the same patient for which the reference plan was performed. The new treatment plan can be for a different patient than for which the reference plan was performed. The operations may also include receiving at least one updated medical image, determining an updated structure set for the updated medical image or receiving an updated structure set, determining a difference between the updated structure set and a structure set included with the reference treatment plan, and determining modified control point information based on the difference using a segment aperture morphing algorithm and using the modified control point information for the warm start optimization. Receiving an updated medical image can include receiving an updated medical image from the same patient for which the reference plan was performed. Receiving an updated medical image can include receiving an updated medical image for a different patient than for which the reference plan was performed. The reference treatment plan can be based on a predetermined plan template and the new treatment plan can be for a different patient than for which the reference plan was performed. The control point information can include shapes of a set of multileaf collimator apertures through which the plurality radiation beams can be modulated. The one or more dose constraints can include a limitation on radiation dosage received by one or more organs at risk (OARs). The at least one beam modulation property of the new treatment plan can include shapes of a set of optimized multileaf collimator apertures through which the plurality of radiation beams can be modulated. The at least one beam modulation property of the new treatment plan can include weighting factors respectively associated with the optimized multileaf collimator apertures in the set, and the weighting factors can indicate relative proportions of radiation doses, such as to be delivered through the respective optimized multileaf collimator apertures.

Certain embodiments of the present disclosure relate to a method for performing radiotherapy treatment planning. The method may be implemented by at least one processor device executing computer-executable instructions. The method may include receiving a reference treatment plan that can include one or more dose constraints and control point information. The method may also include receiving at least one medical image and a structure set not included with the received reference treatment plan. The method may also include determining a new treatment plan, such as based on the received at least one medical image and structure set. The method may also include determining, such as based on the reference treatment plan, control point information of a plurality of radiation beams and registering the plurality of radiation beams to the received at least one medical image. The method may also include determining an optimized fluence map for each of the plurality of radiation beams, such as based on the one or more dose constraints that can be included in the reference treatment plan, such as by using a fluence map optimization algorithm and the received at least one medical image and structure set. The method may also include determining an optimized dose distribution, such as based on the optimized fluence maps of the plurality of radiation beams. The method may also include determining at least one beam modulation property of the new treatment plan, such as by using a warm-start optimization algorithm, such as based on the control point information that can be included in the reference treatment plan by optimizing shapes and/or weights of the control points and/or weights of the plurality of radiation beams, such as to achieve the optimized dose distribution. The new treatment plan can be for the same patient for which the reference plan was performed. The new treatment plan can be for a different patient than for which the reference plan was performed. The method may also include receiving at least one updated medical image, determining an updated structure set for the updated medical image or receiving an updated structure set, determining a difference between the updated structure set and a structure set that can be included with the reference treatment plan, and determining modified control point information, such as based on the difference using a segment aperture morphing algorithm and using the modified control point information for the warm start optimization. An updated medical image can include receiving an updated medical image from the same patient for which the reference plan was performed. Receiving an updated medical image can include receiving an updated medical image for a different patient than for which the reference plan was performed. The reference treatment plan can be based on a predetermined template and the new treatment plan can be for a different patient than for which the reference plan was performed. The control point information can include shapes of a set of multileaf collimator apertures through which the plurality of radiation beams can be modulated. The one or more dose constraints can include a limitation on radiation dosage received by one or more organs at risk (OARs). The at least one beam modulation property of the new treatment plan can include shapes of a set of optimized multileaf collimator apertures through which the plurality of radiation beams can be modulated. The at least one beam modulation property of the new treatment plan can include weighting factors respectively associated with the optimized multileaf collimator apertures in the set, the weighting factors can indicate relative proportions of radiation doses, such as can be delivered through the respective optimized multileaf collimator apertures.

Certain embodiments of the present disclosure relate to a non-transitory computer-readable medium that stores a set of instructions that is executable by at least one processor of a device to cause the device to perform a method for radiotherapy treatment planning. The method can include receiving a reference treatment plan. The reference treatment plan can include one or more dose constraints and control point information. The method can also include receiving at least one medical image and a structure set not included with the received reference treatment plan. The method can also include determining a new treatment plan, such as based on the received at least one medical image and structure set. The method can also include determining, such as based on the reference treatment plan, control point information of a plurality of radiation beams and registering the plurality of radiation beams to the received at least one medical image. The method can also include determining an optimized fluence map for each of the plurality of radiation beams based on the one or more dose constraints included in the reference treatment plan, such as by using a fluence map optimization algorithm and the received at least one medical image and structure set. The method can also include determining an optimized dose distribution, such as based on the optimized fluence maps of the plurality of radiation beams. The method can also include determining at least one beam modulation property of the new treatment plan using a warm-start optimization algorithm, such as based on the control point information included in the reference treatment plan, such as by optimizing shapes and/or weights of the control points and/or weights of the plurality of radiation beams, such as to achieve the optimized dose distribution. The new treatment plan can be for the same patient for which the reference plan was performed. The new treatment plan can be for a different patient than for which the reference plan was performed. The method can also include receiving at least one updated medical image, determining an updated structure set for the updated medical image or receiving an updated structure set, determining a difference between the updated structure set and a structure set included with the reference treatment plan, and determining modified control point information, such as based on the difference using a segment aperture morphing algorithm and using the modified control point information for the warm start optimization. Receiving an updated medical image can include receiving an updated medical image from the same patient for which the reference plan was performed. Receiving an updated medical image includes receiving an updated medical image for a different patient than for which the reference plan was performed.

Certain embodiments of the present disclosure relate to a radiotherapy system. The radiotherapy system may include a memory device storing computer-executable instructions. The radiotherapy system may also include at least one processor device communicatively coupled to the memory device. The computer-executable instructions, when executed by the at least one processor device, may cause the processor device to perform various operations for radiotherapy planning. The operations may include receiving reference treatment planning information including one or more dose constraints for targets and/or OARs and receiving, based on the reference treatment plan, the initial control point information for a plurality of radiation beams. The reference treatment plan may be based on a medical image of a patient obtained in a prior treatment session. The operations may also include receiving an updated medical image of the patient obtained after the prior treatment session. The operations may also include determining a difference between the updated medical image and the medical image obtained in the prior treatment session. The operations may also include determining modified control point information based on the difference using an aperture morphing algorithm. The operations may also include determining a fluence map for each of the plurality of radiation beams based on the one or more dose constraints using a fluence map optimization algorithm. The operations may also include determining a dose distribution based on the fluence maps of the plurality of radiation beams. In addition, the operations may include further modification of at least one control point property and obtaining a new treatment plan using a warm-start optimization algorithm based on this modified control point information and the fluence map dose distribution. In addition, the radiotherapy system may include a radiotherapy device including a linear accelerator configured to deliver radiation to the patient according to the new radiation treatment plan.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

The foregoing general description and the following detailed description are exemplary and explanatory only, and are not restrictive.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items. And the singular forms "a," "an," and "the" are intended to include plural references, unless the context clearly dictates otherwise.

Systems and methods consistent with the present disclosure are directed to radiation therapy or radiotherapy. As used herein, the terms "radiation therapy," "radiotherapy," and "radiation oncology" are used interchangeably. In particular, embodiments of the present disclosure may be applicable in several specific radiotherapy techniques, such as intensity-modulated radiation therapy (IMRT) and image-guided radiation therapy (IGRT).

IMRT is a method in which radiation doses are delivered through "modulated" radiation beams. This modulation is accomplished by means of a device known as a multileaf collimator (MLC) attached to a radiation source or radiation head (e.g., the radiation head of a LINAC). The MLC has adjustable leaves (often made of heavy-metal materials) that act as a filter, blocking or allowing radiation through in a precise manner controlled by a computer, in order to tailor the beam shape to the shape of the target volume while minimizing exposure of the neighboring OARs.

IGRT refers to a technique of using frequent 2D or 3D imaging to direct radiotherapy during a course of radiation treatment (e.g., inter-fractional or intra-fractional). IGRT technique may be used to improve the accuracy of radiation field placement, and to reduce the exposure of healthy tissue during radiation treatments.

In some embodiments, a radiotherapy system may adopt either the IMRT or the IGRT technique. In other embodiments, a radiotherapy system may adopt both techniques.

Figure 1A:
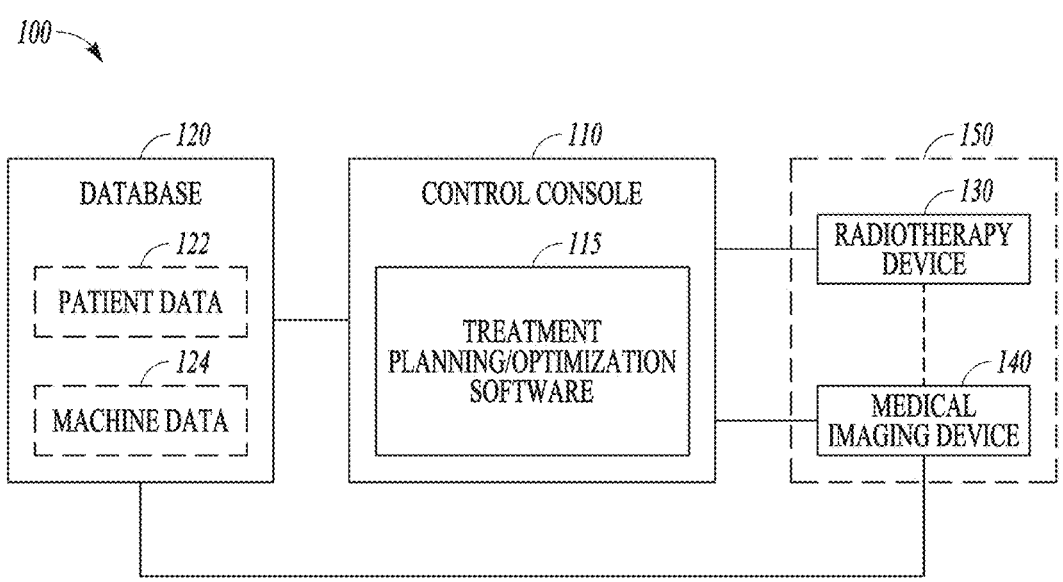
FIG. 1A illustrates an exemplary radiotherapy system, according to some embodiments of the present disclosure.

FIG. 1A illustrates an exemplary radiotherapy system 100, according to some embodiments of the present disclosure. Radiotherapy system 100 may include an IMRT system, an IGRT system, or both. As shown in FIG. 1A, radiotherapy system 100 may include a control console 110, a database 120, a radiotherapy device 130, and a medical imaging device 140. In some embodiments, radiotherapy device 130 and medical imaging device 140 may be integrated into a single image-guided radiotherapy device 150, as indicated by the dashed box 150 in FIG. 1A. In some embodiments, radiotherapy device 130 and medical imaging device 140 may be separate devices. In some embodiments, radiotherapy device 130 and medical imaging device 140 may be physically or communicative connected to each other, as indicated by a dotted-dashed line between radiotherapy device 130 and medical imaging device 140 in FIG. 1A.

Control console 110 may include hardware and software components to control radiotherapy device 130 and/or medical imaging device 140, and/or to perform functions or operations such as treatment planning, treatment execution, medical image acquisition, image processing, motion tracking, motion management, or other tasks involved in a radiotherapy process. The hardware components may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. The software components may include operating system software, application software, etc. For example, as shown in FIG. 1A, control console 110 may include treatment planning/optimization software 115 that may be stored in a memory/storage device of control console 110. Software 115 may include computer readable and executable codes or instructions. A processor device of control console 110 may be communicatively connected to the memory/storage device storing software 115 to access and execute the codes or instructions. The execution of the codes or instructions may cause the processor device to perform operations to achieve one or more functions consistent with the disclosed embodiments.

Control console 110 may be communicatively connected to database 120 to access data. In some embodiments, database 120 may be implemented using local hardware devices, such as one or more hard drives, optical disks, and/or servers that are in the proximity of control console 110. In some embodiments, database 120 may be implemented in a data center or a server located remotely with respect to control console 110. Control console 110 may access data stored in database 120 through wired or wireless communication.

Database 120 may include patient data 122. Patient data may include information such as imaging data associated with a patient (e.g., MRI, CT, X-ray, PET, SPECT, and the like); anatomical region, organ, or volume of interest segmentation data; functional organ modeling data (e.g., serial versus parallel organs, and appropriate dose response models); radiation dosage data (e.g., may include dose-volume histogram (DVH) information); lab data (e.g., hemoglobin, platelets, cholesterol, triglycerides, creatinine, sodium, glucose, calcium, weight); vital signs (blood pressure, temperature, respiratory rate and the like); genomic data (e.g., genetic profiling); demographics (age, sex, ethnicity, etc.); other diseases affecting the patient (e.g., cardiovascular disease, respiratory disease, diabetes, radiation hypersensitivity syndromes, and the like); medications and drug reactions; diet and lifestyle (e.g., smoking or non-smoking); environmental risk factors; tumor characteristics (histological type, tumor grade, hormone and other receptor status, tumor size, vascularity cell type, cancer staging, Gleason score, etc.); previous treatments (e.g., surgeries, radiation, chemotherapy, hormone therapy, etc.); lymph node and distant metastases status; genetic/protein biomarkers (e.g., MYC, GADD45A, PPM1D, BBC3, CDKNIA, PLK3, XPC, AKT1, RELA, BCL2L1, PTEN, CDK1, XIAP, and the like); single nucleotide polymorphisms (SNP) analysis (e.g., XRCC1, XRCC3, APEX1, MDM2, TNFR, MTHFR, MTRR, VEGF, TGFβ, TNFα, etc.), and the like.

Database 120 may also include machine data 124. Machine data 124 may include information associated with radiotherapy device 130, medical imaging device 140, or other machines relevant to radiotherapy, such as radiation beam size, arc placement, on/off time duration, coordinate system, multi-leaf collimator (MLC) configuration, MRI pulse sequence, and the like.

Medical imaging device 140 may provide medical images of a patient. For example, medical imaging device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, medical imaging device 140 may include an MRI imaging device, a CT imaging device, a PET imaging device, an ultrasound imaging device, a fluoroscopic device, a SPECT imaging device, or other medical imaging devices for obtaining the medical images of the patient. As shown in FIG. 1A, medical imaging device 140 may be communicatively connected with database 120 to store medical images to database 120.

Radiotherapy device 130 may include a LINAC or other suitable devices capable of delivering radiation to an anatomical region of interest of a patient in a controllable manner.

Figure 1B:
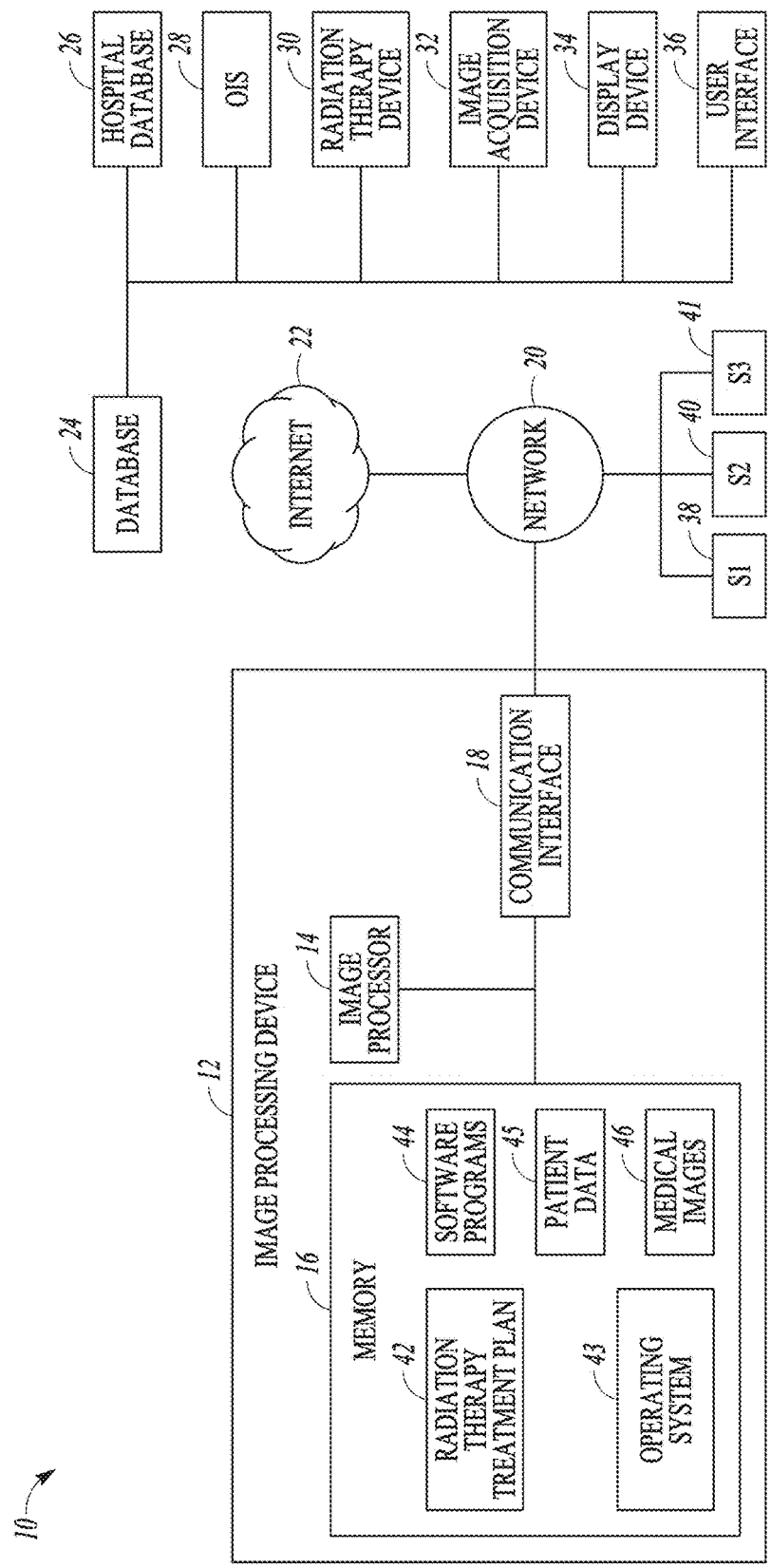
FIG. 1B illustrates an exemplary radiotherapy system, according to some embodiments of the present disclosure.

FIG. 1B illustrates an exemplary radiotherapy system 10 for providing radiation therapy to a patient. The radiotherapy system 10 includes an image processing device, 12. The image processing device 12 may be connected to a network 20. The network 20 may be connected to the Internet 22. The network 20 can connect the image processing device 12 with one or more of a database 24, a hospital database 26, an oncology information system (OIS) 28, a radiation therapy device 30, an image acquisition device 32, a display device 34, and a user interface 36. The image processing device 12 is configured to generate radiation therapy treatment plans 16 to be used by the radiation therapy device 30.

The image processing device 12 may include a memory device 16, a processor 14 and a communication interface 18. The memory device 16 may store computer-executable instructions, such as an operating system 43, a radiation therapy treatment plans 42 (e.g., original treatment plans, adapted treatment plans and the like), software programs 44 (e.g., artificial intelligence, deep learning, neural networks, and radiotherapy treatment plan software), and any other computer-executable instructions to be executed by the processor 14. In an embodiment the software programs 44 may be convert medical images of one format (e.g., MRI) to another format (e.g., CT) by producing synthetic images, such as a pseudo-CT image. For instance, the software programs 44 may include image processing programs to train a predictive model for converting a medial image 46 in one modality (e.g., an MRI image) into a synthetic image of a different modality (e.g., a pseudo CT image); alternatively, the trained predictive model may convert a CT image into an MRI image. The memory device 16 may store data, including medical images 46, patient data 45, and other data required to create and implement a radiation therapy treatment plan 42.

In addition to the memory 16 storing the software programs 44, it is contemplated that software programs 44 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 44 when downloaded to image processing device 14 may be executed by image processor 14.

The processor 14 may be communicatively coupled to the memory device 16, and the processor 14 may be configured to execute computer executable instructions stored thereon. The processor 14 may send or receive medical images 46 to memory 16. For example, the processor 14 may receive medical images 46 from the image acquisition device 32 via the communication interface 18 and network 18 to be stored in memory 16. The processor 14 may also send medical images 46 stored in memory 16 via the communication interface 18 to the network 20 be either stored in database 24 or the hospital database 26.

Further, the processor 14 may utilize software programs 44 (e.g., a treatment planning software) along with the medical images 46 and patient data 45 to create the radiation therapy treatment plan 42. Medical images 46 may include information such as imaging data associated with a patient anatomical region, organ, or volume of interest segmentation data. Patient data 45 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 14 may utilize software programs to generate intermediate data such as updated parameters to be used, for example, by a neural network model; or generate intermediate 2D or 3D image, which may then subsequently be stored in memory 16. The processor 14 may subsequently then transmit the executable radiation therapy treatment plan 42 via the communication interface 18 to the network 20 to the radiation therapy device 30, where the radiation therapy plan will be used to treat a patient with radiation. In addition, the processor 14 may execute software programs 44 to implement functions such as image conversion, image segmentation, deep learning, neural networks, and artificial intelligence. For instance, the processor 14 may execute software programs 44 that train or contour a medical image; such software 44 when executed may train a boundary detector, utilize a shape dictionary.

The processor 14 may be a processing device, include one or more general-purpose processing devices such as a microprocessor, a central processing unit (CPU), a graphics processing unit (GPU), an accelerated processing unit (APU), or the like. More particularly, the processor 14 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 14 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 14 may be a special-purpose processor, rather than a general-purpose processor. The processor 14 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 14 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 14 may also include accelerated processing units such as the Desktop A-4(6,8) Series manufactured by AMD™, the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 14 can execute sequences of computer program instructions, stored in memory 16, to perform various operations, processes, methods that will be explained in greater detail below.

The memory device 16 can store medical images 46. In some embodiments, the medical images 46 may include one or more MRI image (e.g., 2D MRI, 3D MRI, 2D streaming MRI, 4D MRI, 4D volumetric MRI, 4D cine MRI, etc), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 46 may also include medical image data, for instance, training images, and ground truth images, contoured images. In an embodiment, the medical images 46 may be received from the image acquisition device 32. Accordingly, image acquisition device 32 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 46 may be received and stored in any type of data or any type of format that the image processing device 12 may use to perform operations consistent with the disclosed embodiments. The memory device 12 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 14, or any other type of computer device. The computer program instructions can be accessed by the processor 14, read from the ROM, or any other suitable memory location, and loaded into the RAM for execution by the processor 14. For example, the memory 16 may store one or more software applications. Software applications stored in the memory 16 may include, for example, an operating system 43 for common computer systems as well as for software-controlled devices. Further, the memory 16 may store an entire software application, or only a part of a software application, that are executable by the processor 14. For example, the memory device 16 may store one or more radiation therapy treatment plans 42.

The image processing device 12 can communicate with the network 20 via the communication interface 18, which is communicatively coupled to the processor 14 and the memory 16. The Communication interface 18 may provide communication connections between the image processing device 12 and radiotherapy system 10 components (e.g., permitting the exchange of data with external devices). For instance the communication interface 18 may in some embodiments have appropriate interfacing circuitry to connect to the user interface 36, which may be a hardware keyboard, a keypad, or a touch screen through which a user may input information into radiotherapy system 10.

Communication interface 18 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 18 may include one or more digital and/or analog communication devices that permit image processing device 12 to communicate with other machines and devices, such as remotely located components, via the network 20.

The network 20 may provide the functionality of a local area network (LAN), a wireless network, a cloud computing environment (e.g., software as a service, platform as a service, infrastructure as a service, etc.), a client-server, a wide area network (WAN), and the like. For example, network 20 may be a LAN or a WAN that may include other systems S1 (38), S2 (40), and S3(41). Systems S1, S2, and S3 may be identical to image processing device 12 or may be different systems. In some embodiments, one or more of systems in network 20 may form a distributed computing/simulation environment that collaboratively performs the embodiments described herein. In some embodiments, one or more systems S1, S2, and S3 may include a CT scanner that obtain CT images (e.g., medical images 46). In addition, network 20 may be connected to internet 22 to communicate with servers and clients that reside remotely on the internet.

Therefore, network 20 can allow data transmission between the image processing device 12 and a number of various other systems and devices, such as the OIS 28, the radiation therapy device 30, and the image acquisition device 32. Further, data generated by the OIS 28 and/or the image acquisition device 32 may be stored in the memory 16, the database 24, and/or the hospital database 26. The data may be transmitted/received via network 20, through communication interface 18 in order to be accessed by the processor 14, as required.

The image processing device 12 may communicate with database 24 through network 20 to send/receive a plurality of various types of data stored on database 24. For example database 24 may include machine data that is information associated with a radiation therapy device 30, image acquisition device 32, or other machines relevant to radiotherapy. Machine data information may include radiation beam size, arc placement, beam on and off time duration, control points, segments, multi-leaf collimator (MLC) configuration, gantry speed, MRI pulse sequence, and the like. Database 24 may be a storage device. One skilled in the art would appreciate that database 24 may include a plurality of devices located either in a central or a distributed manner.

In some embodiments, database 24 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 14 may communicate with database 24 to read images into memory 16 or store images from memory 16 to database 24. For example, the database 24 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 24 received from image acquisition device 32. Database 24 may store data to be used by the image processor 14 when executing software program 44, or when creating radiation therapy treatment plans 42. The image processing device 12 may receive the imaging data 46 (e.g., 2D MRI slice images, CT images, 2D Fluoroscopy images, X-ray images, 3DMRI images, 4D MRI images, etc.) either from the database 24, the radiation therapy device 30 (e.g., a MRI-Linac), and or the image acquisition device 32 to generate a treatment plan 42.

In an embodiment, the radiotherapy system 100 can include an image acquisition device 32 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 32 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 32 can be stored within database 24 as either imaging data and/or test data. By way of example, the images acquired by the imaging acquisition device 32 can be also stored by the image processing device 12, as medical image data 46 in memory 16.

In an embodiment, for example, the image acquisition device 32 may be integrated with the radiation therapy device 30 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 42 to a predetermined target.

The image acquisition device 32 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 32 can acquire a 2D slice in any orientation. For example, an orientation of the 2D slice can include a sagittal orientation, a coronal orientation, or an axial orientation. The processor 14 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 32 in "real-time" while a patient is undergoing radiation therapy treatment, for example, when using the radiation therapy device 30. "Real-time" meaning acquiring the data in at least milliseconds or less.

The image processing device 12 may generate and store radiation therapy treatment plans 42 for one or more patients. The radiation therapy treatment plans 42 may provide information about a particular radiation dose to be applied to each patient. The radiation therapy treatment plans 42 may also include other radiotherapy information, such as beam angles, dose-histogram-volume information, the number of radiation beams to be used during therapy, the dose per beam, and the like.

The image processor 14 may generate the radiation therapy treatment plan 42 by using software programs 44 such as treatment planning software, such as Monaco®, manufactured by Elekta AB of Stockholm, Sweden. In order to generate the radiation therapy treatment plans 42, the image processor 14 may communicate with the image acquisition device 32 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the treatment planning device 110 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 32 to reveal the internal structure of a body part. Based on the information from the medical images, a 3D structure of the relevant anatomical portion may be obtained. The obtained 3D structure of the relevant anatomical portion may be stored as an anatomical structure set, for example, in accordance with the DICOM grayscale imaging standard for medical imaging. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and ≤54 Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 12 can generate a tailored radiation therapy treatment plan 42 having these parameters in order for the radiation therapy device 30 to provide radiotherapy treatment to the patient.

In addition, the radiotherapy system 10 may include a display device 34 and a user interface 36. The display device 34 may include one or more display screens that display medical images, interface information, treatment planning parameters (e.g., contours, dosages, beam angles, etc.) treatment plans, a target, localizing a target and/or tracking a target, or any related information to the user. The user interface 36 may be a keyboard, a keypad, a touch screen or any type of device that a user may input information to radiotherapy system 10. Alternatively, the display device 34 and the user interface 36 may be integrated into a device such as a tablet computer, e.g., Apple iPad®, Lenovo Thinkpad®, Samsung Galaxy®, etc.

Furthermore, any and all components of the radiotherapy system 10 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 12, the OIS 28, the image acquisition device 32 could be implemented as a virtual machine. Given the processing power, memory, and computational capability available, the entire radiotherapy system 10 could be implemented as a virtual machine.

Figure 2A:
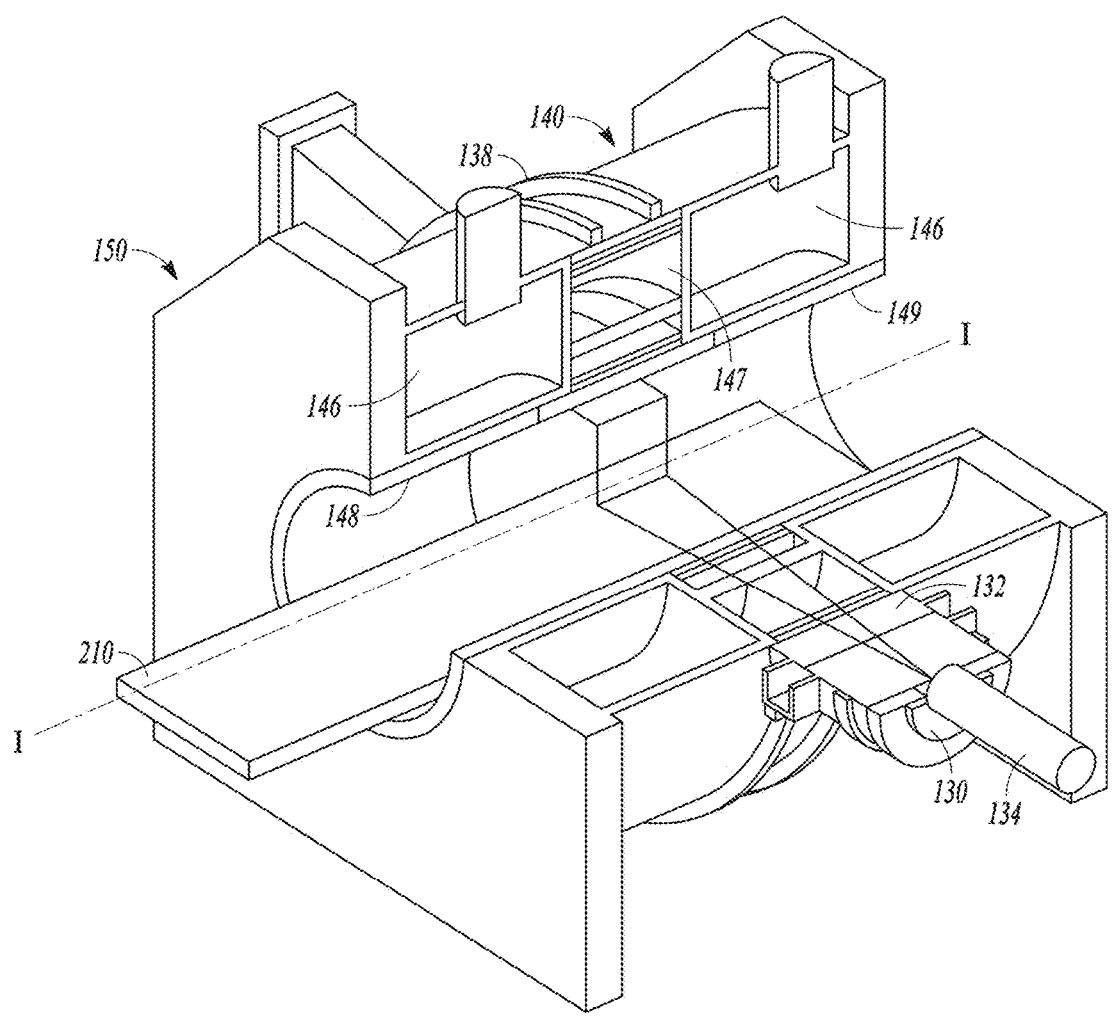
FIG. 2A illustrates an exemplary radiotherapy device, according to some embodiments of the present disclosure.

FIG. 2A illustrates an exemplary image-guided radiotherapy device 150, according to some embodiments of the present disclosure. Device 150 includes a couch 210, a medical image acquisition portion corresponding to medical imaging device 140, and a radiation delivery portion corresponding to radiotherapy device 130.

Couch 210 may be used for supporting a patient (not shown) during a treatment session, and may also be referred to as a patient supporting system. Couch 210 may be movable along a horizontal, translation axis (labelled "I"), such that the patient resting on couch 210 can be moved into and/or out of device 150. In some embodiments, couch 210 may be rotatable around a central vertical axis of rotation, transverse to the translation axis. Couch 210 may be motorized to move in various directions and rotate along various axes to properly position the patient according to a treatment plan.

Medical imaging device 140 may include an MRI machine used to acquire 2D or 3D MRI images of a patient before, during, and/or after a treatment session. Medical imaging device 140 may include a magnet 146 for generating a primary magnetic field for magnetic resonance imaging. The magnetic field lines generated by operation of magnet 146 may run substantially parallel to the central translation axis I. Magnet 146 may include one or more coils with an axis that runs parallel to the translation axis I. In some embodiments, the one or more coils in magnet 146 may be spaced such that a central window 147 of magnet 146 is free of coils. In other embodiments, the coils in magnet 146 may be thin enough or of a reduced density such that they are substantially transparent to radiation of the wavelength generated by radiotherapy device 130. Medical imaging device 140 may also include one or more active shielding coils, which may generate a magnetic field outside magnet 146 of approximately equal magnitude and opposite polarity to cancel the magnetic field outside magnet 146. A radiation source 134 of radiotherapy device 130 may be positioned in the region where the magnetic field is cancelled, at least to a first order.

Medical imaging device 140 may also include two gradient coils 148 and 149, which may generate a gradient magnetic field that is superposed on the primary magnetic field. Coils 148 and 149 may generate a gradient in the resultant magnetic field that allows spatial encoding of the protons so that their position can be determined. Gradient coils 148 and 149 may be positioned around a common central axis with the magnet 146, and may be displaced from on another along that central axis. The displacement may create a gap, or window, between coils 148 and 149. In the embodiments wherein magnet 146 also includes a central window 147 between coils, the two windows may be aligned with each other.

Radiotherapy device 130 may include the source of radiation 134, such as an X-ray source or a linear accelerator, and a multi-leaf collimator (MLC) 132. Radiotherapy device 130 may be mounted on a chassis 138. Chassis 138 may be continuously rotatable around couch 210 when it is inserted into the treatment area, powered by one or more chassis motors. A radiation detector may also be mounted on chassis 138 if desired, preferably opposite to radiation source 134 and with the rotational axis of chassis 138 positioned between radiation source 134 and the detector. The control circuitry of radiotherapy device 130 may be integrated within device 150 or remote from it, and is functionally represented by control console 110 of FIG. 1A.

During a radiotherapy treatment session, a patient may be positioned on couch 210, which may be inserted into the treatment area defined by magnetic coils 146, 148, 149, and chassis 138. Control console 110 may control radiation source 134, MLC 132, and the chassis motor(s) to deliver radiation to the patient through the window between coils 148 and 149. In some embodiments, image acquisition device 140 may correspond to image acquisition device 32 in FIG. 1B that may acquire origin images of a first modality (e.g., MRI image shown in FIG. 2D) or destination images of a second modality (e.g., CT image shown in FIG. 2E).

Figure 2B:
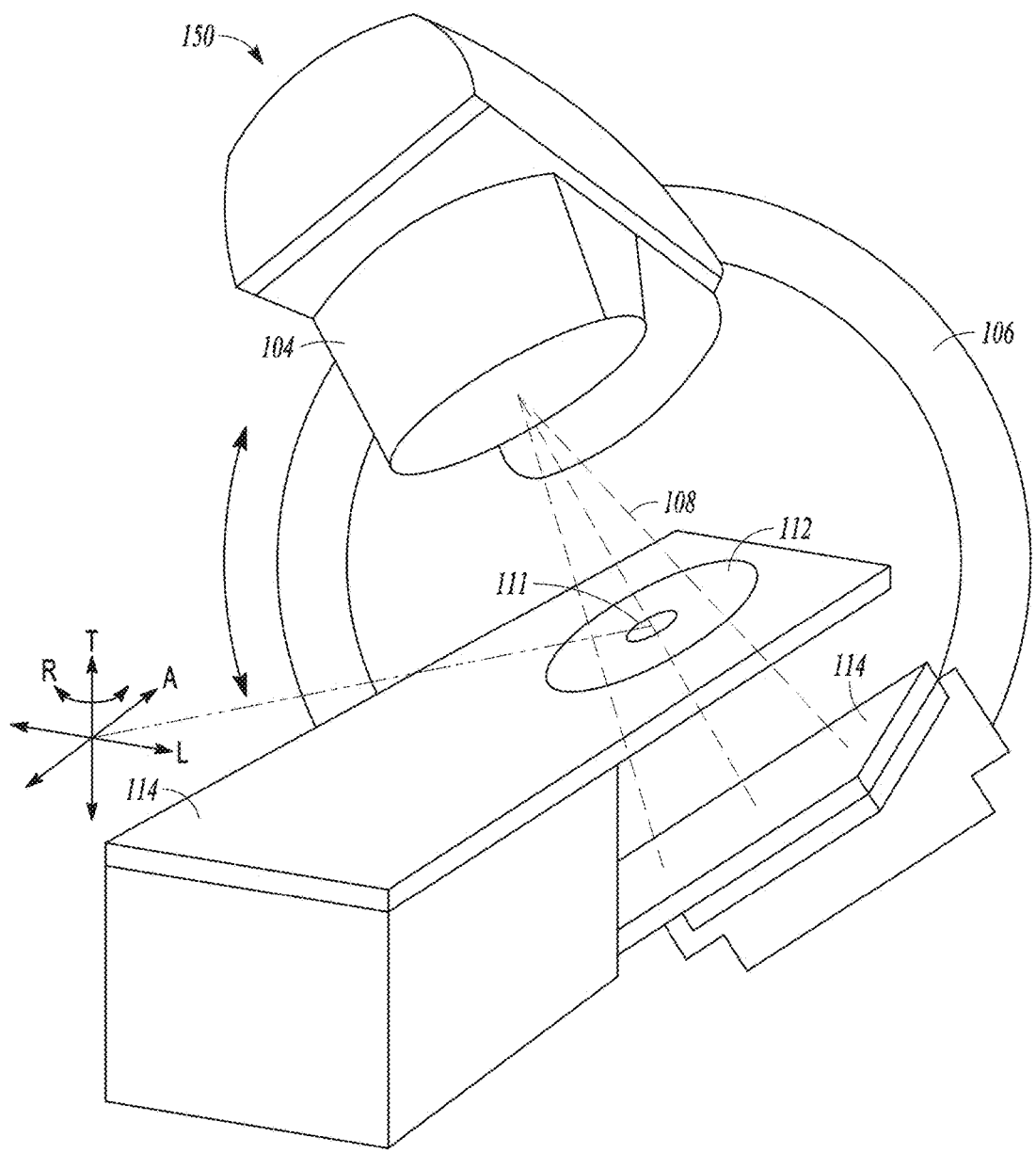
FIG. 2B illustrates another exemplary radiotherapy device, according to some embodiments of the present disclosure.

FIG. 2B illustrates an exemplary radiation therapy device 150 may include a radiation source, such as an X-ray source or a linear accelerator, a multi-leaf collimator (not shown), a couch 116, an imaging detector 114, and a radiation therapy output 104. The radiation therapy device 150 may be configured to emit a radiation beam 108 to provide therapy to a patient. The radiation therapy output 104 can include one or more attenuators or collimators, such as a multi-leaf collimator (MLC) as described in the illustrative example of FIG. 2F, below.

Referring back to FIG. 2B, a patient can be positioned in a region 112, using a table or couch 116 to receive a radiation therapy dose according to a radiation therapy treatment plan. The radiation therapy output 104 can be mounted or attached to a gantry 106 or other mechanical support. One or more chassis motors (not shown) may rotate the gantry 106 and the radiation therapy output 104 around couch 116 when the couch 116 is inserted into the treatment area. In an embodiment, gantry 106 may be continuously rotatable around couch 116 when the couch 116 is inserted into the treatment area. In another embodiment, gantry 106 may rotate to a predetermined position when the couch 116 is inserted into the treatment area. For example, the gantry 106 can be configured to rotate the therapy output 104 around an axis ("A"). Both the couch 116 and the radiation therapy output 104 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more (not shown) may control the couch 116 movements or rotations in order to properly position the patient in or out of the radiation beam 108 position according to a radiation therapy treatment plan. As both the couch 116 and the gantry 106 are independently moveable from one another in multiple degrees of freedom, which allows the patient to be positioned such that the radiation beam 108 precisely can target the tumor.

The coordinate system (including axes A, T, and L) shown in FIG. 2B can have an origin located at an isocenter 111. The isocenter can be defined as a location where the radiation therapy beam 108 intersects the origin of a coordinate axis, such as to deliver a prescribed radiation dose to a location on or within a patient. For example, the isocenter 111 can be defined as a location where the radiation therapy beam 108 intersects the patient for various rotational positions of the radiation therapy output 104 as positioned by the gantry 106 around the axis A.

Gantry 106 may also have an attached imaging detector 114. The imaging detector 114 preferably located opposite to the radiation source 104, and in an example, the imaging detector 114 can be located within a field of the therapy beam 108.

The imaging detector 114 can be mounted on the gantry 106 preferably opposite the radiation therapy output 104, such as to maintain alignment with the therapy beam 108. The imaging detector 114 rotating about the rotational axis as the gantry 106 rotates. In an embodiment, the imaging detector 114 can be a flat panel detector (e.g., a direct detector or a scintillator detector). In this manner, the imaging detector 114 can be used to monitor the therapy beam 108 or the imaging detector 114 can be used for imaging the patient's anatomy, such as portal imaging. The control circuitry of radiotherapy device 150 may be integrated within system 100 or remote from it.

In an illustrative example, one or more of the couch 116, the therapy output 104, or the gantry 106 can be automatically positioned, and the therapy output 104 can establish the therapy beam 108 according to a specified dose for a particular therapy delivery instance. A sequence of therapy deliveries can be specified according to a radiation therapy treatment plan, such as using one or more different orientations or locations of the gantry 106, couch 116, or therapy output 104. The therapy deliveries can occur sequentially, but can intersect in a desired therapy locus on or within the patient, such as at the isocenter 111. A prescribed cumulative dose of radiation therapy can thereby be delivered to the therapy locus while damage to tissue nearby the therapy locus is reduced or avoided.

Figure 2C:
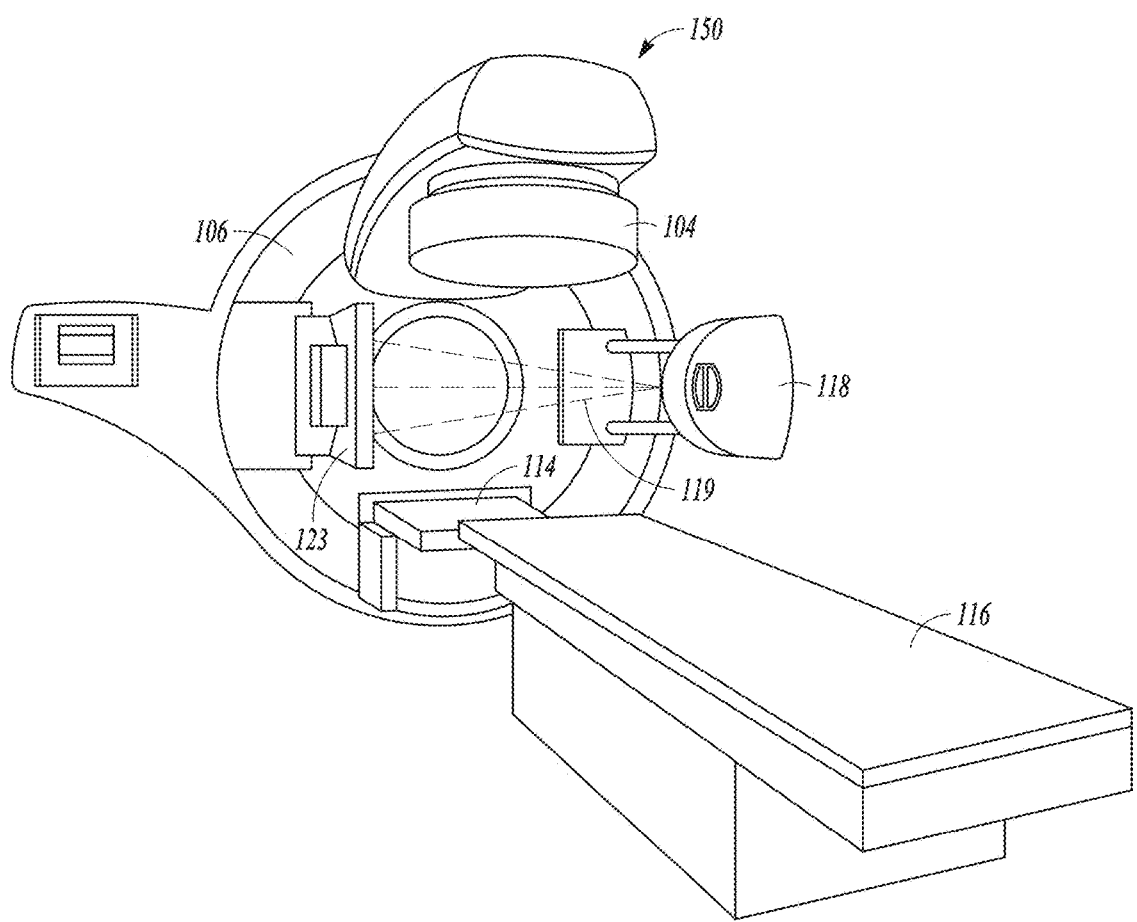
FIG. 2C illustrates an exemplary system including a combined radiation therapy system and an imaging system, such as a computed tomography (CT) imaging system.
Figure 2D:
FIGS. 2D and 2E depict the differences between an exemplary MRI image and a corresponding CT image.
Figure 2E:
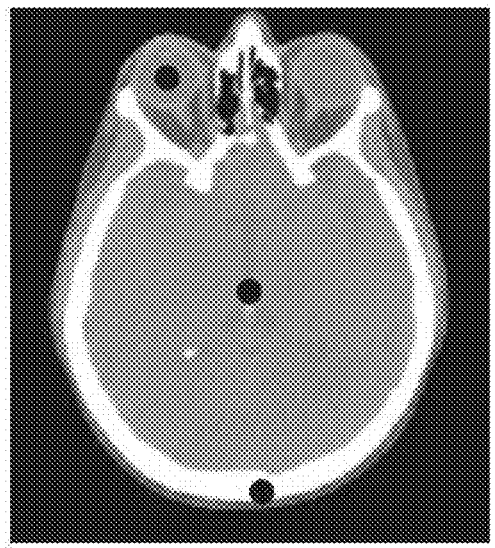

FIG. 2C illustrates an exemplary radiation therapy device 150 that may include combining a linear accelerator and an imaging system, such as can include a computed tomography (CT) imaging system. The CT imaging system can include an imaging X-ray source 118, such as providing X-ray energy in a kiloelectron-Volt (keV) energy range. The imaging X-ray source 118 provide a fan-shaped and/or a conical beam 119 directed to an imaging detector 123, such as a flat panel detector. The radiation therapy system 150 can be similar to the system 150 described in relation to FIG. 2B, such as including a radiation therapy output 104, a gantry 106, a platform 116, and another flat panel detector 114. The X-ray source 118 can provide a comparatively-lower-energy X-ray diagnostic beam, for imaging.

In the illustrative example of FIG. 2C, the radiation therapy output 104 and the X-ray source 118 can be mounted on the same rotating gantry 106, rotationally-separated from each other by 90 degrees. In another example, two or more X-ray sources can be mounted along the circumference of the gantry 106, such as each having its own detector arrangement to provide multiple angles of diagnostic imaging concurrently. Similarly, multiple radiation therapy outputs 104 can be provided. FIG. 2A, FIG. 2B, and FIG. 2C illustrate generally illustrate examples of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 2F:
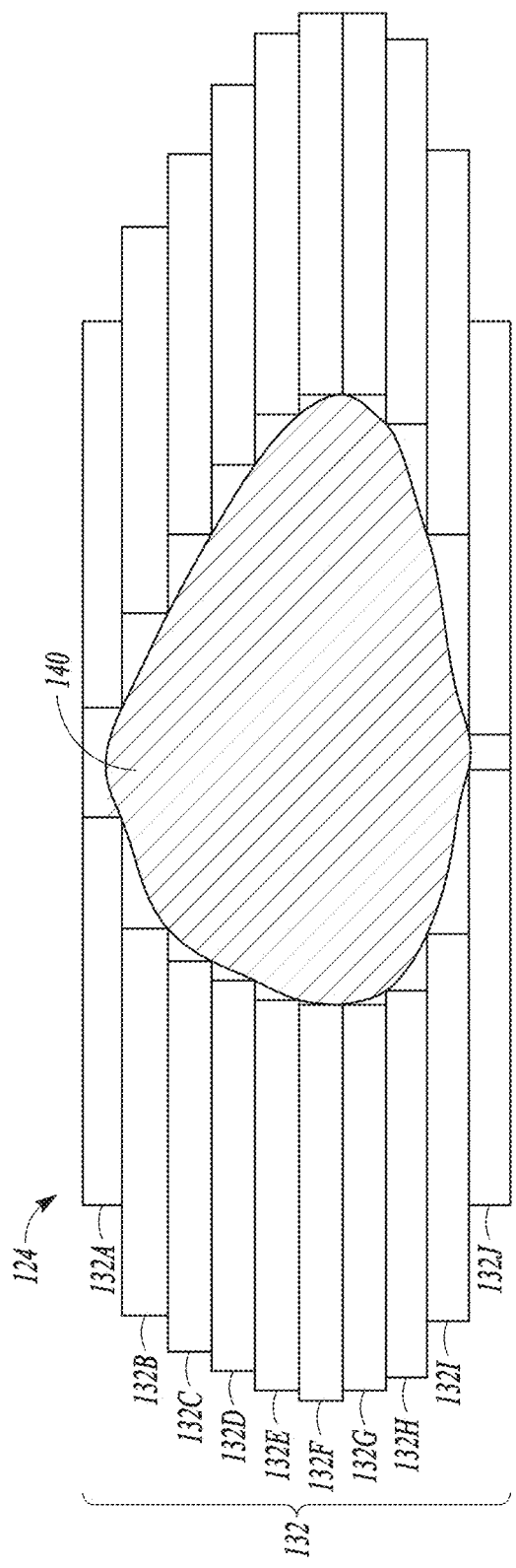
FIG. 2F illustrates an exemplary collimator configuration for shaping, directing, or modulating an intensity of a radiation therapy beam.

As discussed above, radiation therapy devices described by FIG. 2A, FIG. 2B, and FIG. 2C include a multi-leaf collimator for shaping, directing, or modulating an intensity of a radiation therapy beam to the specified target locus within the patient. FIG. 2F illustrates an exemplary multi-leaf collimator (MLC) 132 that includes leaves 132A through 132J that can be automatically positioned to define an aperture approximating a tumor 140 cross section or projection. The leaves 132A through 132J permit modulation of the radiation therapy beam. The leaves 132A through 132J can be made of a material specified to attenuate or block the radiation beam in regions other than the aperture, in accordance with the radiation treatment plan. For example, the leaves 132A through 132J can include metallic plates, such as comprising tungsten, with a long axis of the plates oriented parallel to a beam direction, and having ends oriented orthogonally to the beam direction (as shown in the plane of the illustration of FIG. 2B). A "state" of the MLC 132 can be adjusted adaptively during a course of radiation therapy treatment, such as to establish a therapy beam that better approximates a shape or location of the tumor 140 or other target locus. This is in comparison to using a static collimator configuration or as compared to using an MLC 132 configuration determined exclusively using an "offline" therapy planning technique. A radiation therapy technique using the MLC 132 to produce a specified radiation dose distribution to a tumor or to specific areas within a tumor can be referred to as Intensity Modulated Radiation Therapy (IMRT).

Figure 2G:
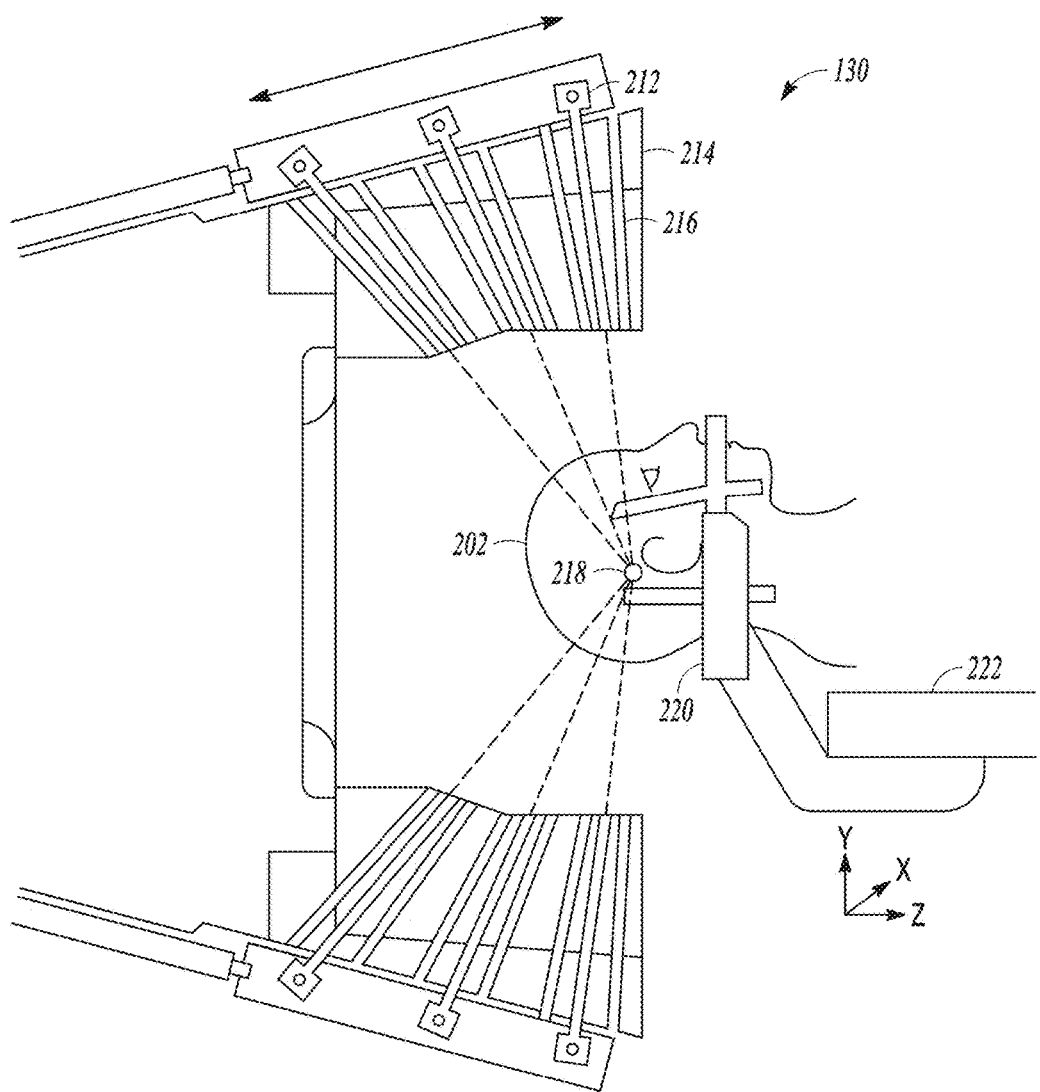
FIG. 2G illustrates an exemplary Gamma knife radiation therapy system.

FIG. 2G illustrates an example of another type of radiotherapy device 130 (e.g., a Leksell Gamma Knife), according to some embodiments of the present disclosure. As shown in FIG. 2G, in a radiotherapy treatment session, a patient 202 may wear a coordinate frame 220 to keep stable the patient's body part (e.g., the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212. Radiation sources 212 may generate a plurality of radiation beams (e.g., beamlets) through beam channels 216. The plurality of radiation beams may be configured to focus on an isocenter 218 from different directions. While each individual radiation beam may have a relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

Figure 3:
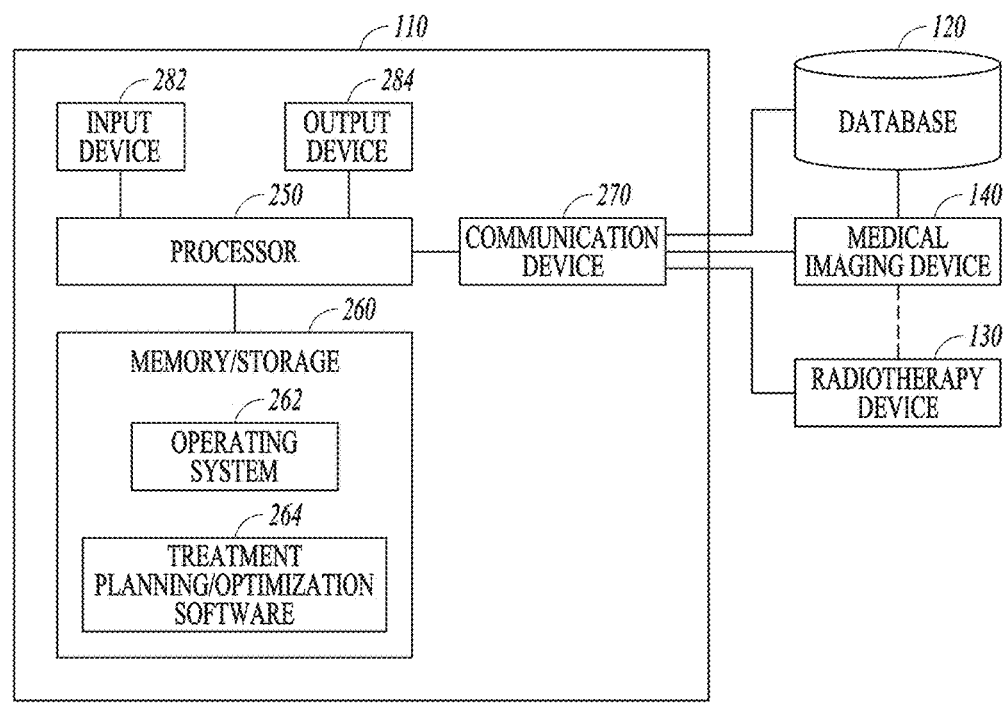
FIG. 3 shows a block diagram of an exemplary control console shown in FIG. 1A.

FIG. 3 illustrates an exemplary control console 110. As shown in FIG. 3, control console 110 may include a processor device 250, a memory or storage device 260, a communication interface 270, an input device 282, and an output device 284. Memory/storage device 260 may store computer executable instructions, such as operating system 262 and treatment planning/optimization software 264. Processor device 250 may be coupled to memory/storage device 260 and configured to execute the computer executable instructions stored thereon. For example, processor device 250 may execute treatment planning/optimization software 264 to implement functionalities such as treatment planning and optimization. Processor device 250 may communicate with database 120 through communication interface 270 to send/receive data to/from database 120. Although only one database 120 is shown in FIG. 3, those skilled in the art would understand that database 120 may include a plurality of devices located either in a central or distributed manner.

Processor device 250 may include one or more general-purpose processing devices such as a microprocessor, central processing unit (CPU), or the like. More particularly, processor device 250 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor device 250 may also be one or more special-purpose processing devices such as an application specific integrated circuit (ASIC), a graphical processing unit (GPU), a field programmable gate array (FPGA), a digital signal processor (DSP), a System on a Chip (SoC), or the like. As would be appreciated by those skilled in the art, in some embodiments, processor device 250 may be a special-purpose processor, rather than a general-purpose processor.

Memory/storage device 260 may include a read-only memory (ROM), a flash memory, a random access memory (RAM), a static memory, a hard drive, etc. In some embodiments, memory/storage device 260 may include a machine-readable storage medium. While the machine-readable storage medium as an exemplary embodiment may be a single medium, the term "machine-readable storage medium" should be taken to include a single medium or multiple media (e.g., a centralized or distributed database, and/or associated caches and servers) that store one or more sets of instructions/data. The term "machine-readable storage medium" shall also be taken to include any medium that is capable of storing or encoding a set of instructions for execution by the machine and that cause the machine to perform any one or more of the methodologies of the present disclosure. The term "machine readable storage medium" shall accordingly be taken to include, but not be limited to, solid-state memories, and optical and magnetic media.

Communication interface 270 may include a network adaptor, a cable connector, a serial connector, a USB connector, a parallel connector, a high-speed data transmission adaptor such as fiber, USB 3.0, thunderbolt, etc., a wireless network adaptor such as WiFi adaptor, telecommunication (3G, 4G/LTE etc.) adaptor, etc. Communication interface 270 may also include communication interface with radiotherapy device 130 and/or medical imaging device 140. Processor device 250 may communicate with database 120, radiotherapy device 130, medical imaging device 140, or other devices or systems via communication interface 270. Input device 282 may include a keyboard, a mouse, a touchscreen, or other suitable devices for receiving information input by a user. Output device 284 may include a display, a printer, or other suitable devices for outputting information to the user.

Figure 4:
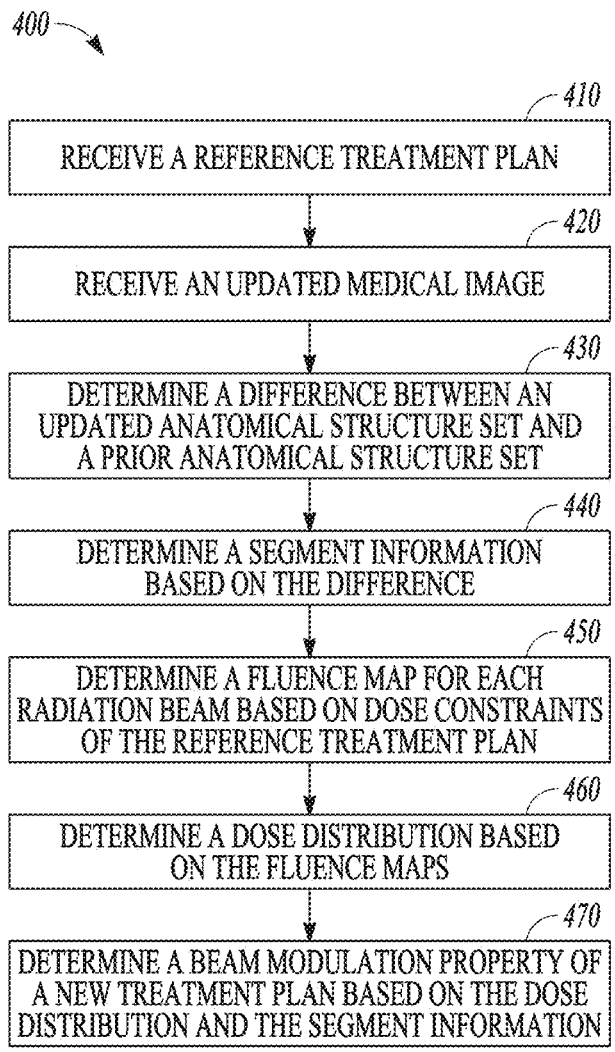
FIG. 4 is a flowchart of an exemplary radiation treatment planning method, according to some embodiments of the present disclosure.

FIG. 4 is a flow chart of an exemplary radiation treatment planning method or workflow 400, according to some embodiments. Method 400 may be used to modify a treatment plan used in a prior treatment session based on one or more medical images acquired after the prior session to account for inter-fractional changes. As used herein, the treatment plan used in the prior treatment session is also referred to as a reference treatment plan. For example, a patient undergoing radiotherapy may receive radiation doses in several sessions. In each session, a fraction of the total dose prescribed by a physician may be administered. The time interval between adjacent sessions may be a day, several days, a week, several weeks, or even several months. As a result, the target of the treatment (e.g., a tumor) may change its size, shape, and/or orientation between sessions, and a treatment plan developed for one session may not be accurate or even acceptable for the next or a later session due to these changes. It is therefore desirable to adapt a treatment plan developed for a prior session to the changes encountered in a new session. In an example, the reference treatment plan can include a DICOM RT Plan.

In step 410, control console 110 may receive a reference treatment plan. The reference treatment plan may be developed for a prior treatment session based on one or more medical images obtained in the prior treatment session. The reference treatment plan may also be developed for a prior treatment session based on at least one structure set obtained in the prior treatment session. The at least one anatomical structure set can include a radiotherapy structure set in accordance with the DICOM grayscale imaging standard for medical imaging. For example, the anatomical structure set can include at least one organ label (e.g. prostate or liver) and associated coordinates that can define a polygon associated with the at least one organ label. The at least one anatomical structure set can be determined based on at least one medical image. The reference treatment plan may include plan parameters such as radiation beam angles (e.g., arc/sub-arc placement) and aperture information (e.g., the shape of the MLC aperture at each beam angle). As used herein, the beam arc/sub-arc placement and aperture information are collectively referred to as control point information.

Figure 5:
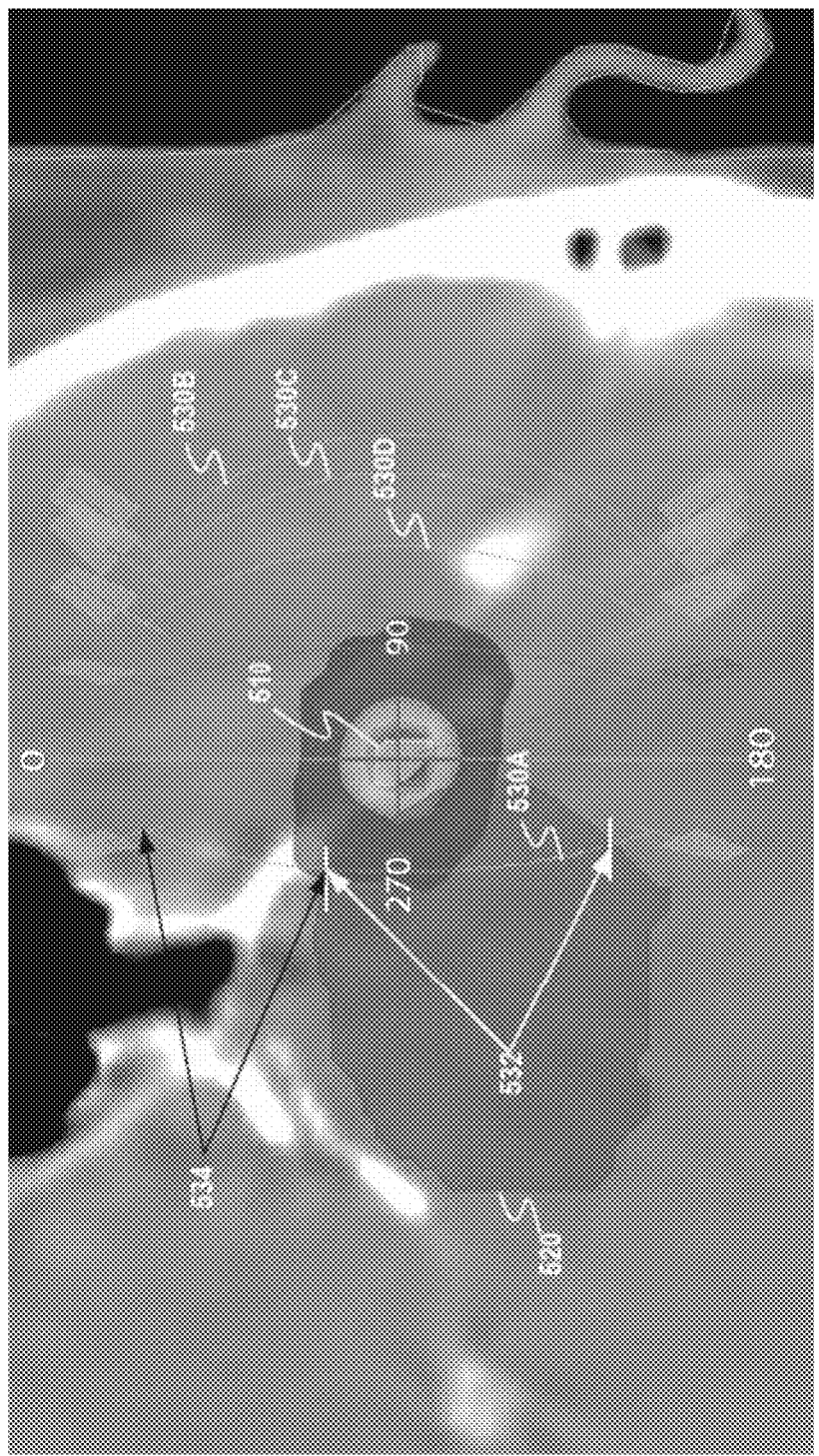
FIG. 5 illustrates an exemplary arc/sub-arc placement, according to some embodiments of the present disclosure.

FIG. 5 illustrates an exemplary beam arc/sub-arc placement with reference to a 2D medical image. In FIG. 5, a target 510 and an OAR 520 may be segmented based on the 2D medical image. The segmentation may be accomplished manually, semi-automatically, or automatically. For example, image segmentation technique may be used (e.g., using control console 110) to delineate target 510 and/or OAR 520. After the target/OAR is delineated, a plurality of radiation beams may be designed such that radiation doses may be applied to target 510 from multiple angles. The radiation beams are often arranged on an arc, which corresponds to a trajectory along which radiation head 245 travels. For example, FIG. 5 shows multiple arcs 530A, 530B, 530C, and 530D, from which radiation may be applied. For example, radiation head 245 may rotate along arc 530A and apply radiation at one or more points along arc 530A. The placement of the arcs may be determined manually or using control console 110 based on the size and location of the target and/or the OAR, the desired dose to be received by the target, the dose-volume constraint to be satisfied with respect to the OAR, and/or any other parameter known to those skilled in the art.

In some embodiments, a weighting factor may be assigned to each arc. The weighting factor may indicate a relative proportion of radiation dose to be delivered along that arc. For example, arc 530A covers a portion of OAR 520. Therefore, the weighting factor assigned to arc 530A may be smaller than the weighting factor assigned to, for example, arc 530B.

In some embodiments, an arc may be further divided into multiple sub-arcs, and each sub-arc may be assigned a separate weighting factor. For example, arc 530A may be divided into two segments: 534 and 532. Because segment 532 covers OAR 520, a smaller weighting factor (or even a zero weighting factor) may be assigned to segment 532 than the weighting factor assigned to segment 534. Because the difference between an undivided arc and a segment is only in terms of their length, for simplicity the term "segment" is used to refers to either an undivided arc or a segment of a divided arc.

Figure 6A:
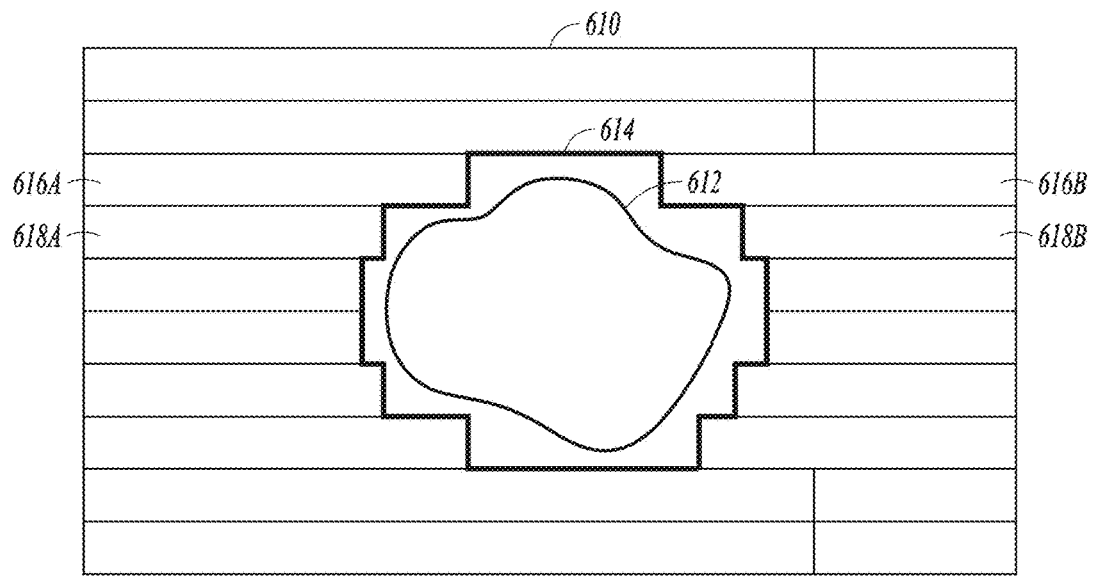
FIGS. 6A-6B illustrate exemplary multileaf collimator apertures, according to some embodiments of the present disclosure.

The arc/segment placement information discussed above characterizes the beam angle or beam direction and is part of the segment information that may be provided by the reference treatment plan. In IMRT, another plan parameter, MLC aperture, may also be part of the segment information. MLC aperture characterizes the beam shape, and is adjustable by moving the leaves of a multileaf collimator. FIG. 6A shows an example MLC configuration 610, including an MLC aperture 614, in bold lines, through which radiation beam is modulated such that the shape of the aperture conforms to the shape of a target 612. As shown in FIG. 6A, the particular shape of aperture 614 can be constructed by a set of leaves 616A, 616B, 618A, 618B, etc. Each leaf may be slab-shaped and can be moved left and right by a actuator mechanism. The leaf may be made of radiation blocking material such that when the two leaves opposite to each other move towards each other, the amount of radiation that can pass through the spacing between the two leaves also decreases. Multiple pairs of leaves may form an aperture, such as aperture 614, based on the shape of the target, such as target 612. In some embodiments, an aperture having a particular shape may be associated with a segment, such that when radiation head 245 moves along the segment, the radiation beam is shaped according to the particular shape of the aperture. In some embodiments, a fixed aperture may be assigned to each segment. In other embodiments, the shape of the aperture may change along a single segment. The aperture information may form part of the segment information that can be provided by the reference plan.

Referring back to FIG. 4, in step 410, control console 110 may receive a reference plan and the reference plan may include segment information of a plurality of radiation beams, such as the segment placement, weighting factors assigned to the segments, and aperture shapes associated with the segments, as discussed above in connection with FIGS. 5 and 6A. The reference plan may also include dose constraints. The dose constraints, also known as dose-volume constraints, may by prescribed by a physician. A typical set of dose constraints is shown in Table 1, as follows:

TABLE 1

A sample dose constraint prescription

| >=95% of Tumor | receives >= 63 Gy |
| <=1% of Tumor | receives >= 72 Gy |
| >=95% of Ext_Tumor | receives >= 60 Gy |
| <=1% of Ext_Tumor | receives >= 70 Gy |
| <=1% of Cord | receives >= 43 Gy |
| <=15% of Heart | receives >= 30 Gy |
| <=50% of Norm_Tissue | receives >= 54 GY |

As shown in Table 1, a dose constraint is assigned to each anatomical region of interest, including that tumor and OARs. The dose constraint is specified by a percentage of number on the left and a threshold value for dose on the right.

The first four lines of the prescription are for a tumor and a so-called extended area around the tumor that is introduced to account for uncertainties about the boundary of the tumor. The first two lines state that the target tumor dose should be higher than a threshold value of 63 Gy for 95% or higher volume of the tumor. On the other hand, the target dose should be below 72 Gy except for a portion of 1% of the tumor volume. The other lines can be similarly interpreted. Dose constraints similar to those shown in Table 1 may be provided in the reference treatment plan.

In step 420, control console 110 may receive an updated medical image, either from medical imaging device 140 or from database 120. The updated medical image may be acquired before a new treatment session starts. The updated medical image may reveal changes of the target (e.g., in size, shape, orientation, etc.) as well as other structures surrounding the target. An updated anatomical structure set can be determined from the updated medical image, and the updated anatomical structure set can be compared against one or more anatomical structure sets obtained during the prior treatment session conducted according to the reference treatment plan to determine a difference between the anatomical structure sets in step 430. Then in step 440, control console 110 may determine segment information based on the difference between the updated anatomical structure set and the anatomical structure set obtained during the prior treatment session. For example, control console 110 may adjust segment information provided by the reference treatment plan according to the difference found in the updated anatomical structure set using a segment aperture morphing (SAM) algorithm. The SAM algorithm may calculate the MLC morphing (leaf shifts) based on the beam's eye view of the new target (new target projection) (NTP) and the beam's eye view of the old target (old target projection) (OTP) for each beam angle and each segment. An exemplary SAM algorithm starts with dividing the old aperture shape into a number of discrete points (boundary points). Then, the coordinates of each boundary point is linearly transformed from OTP to NTP.

Figure 6B:
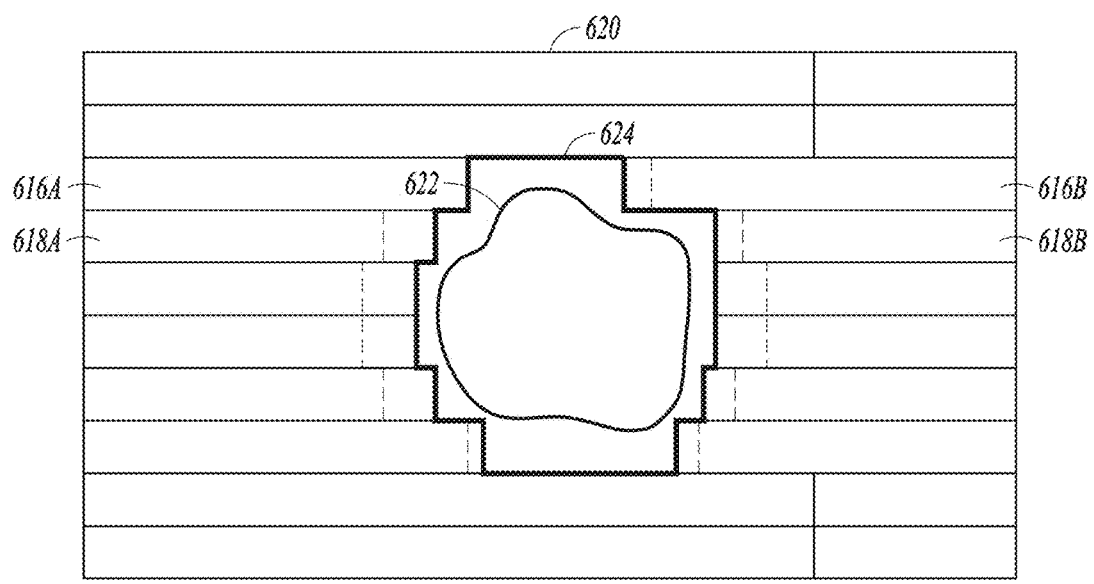

FIG. 6B shows an exemplary MLC configuration 620 adapted to a changed target 622. Referring to FIG. 6B, target 622 becomes smaller compared to target 612, and the shape of the target also changes. To account for the changes, some leaves are shifted (e.g., 618A, 616B, 618B, where the old position of the leaves are shown in dashed lines) to form a new aperture 624 (shown in bold lines). The new aperture 624 may be determined (e.g., through SAM) as part of the segment information in step 440.

Referring back to FIG. 4, control console 110 may determine a fluence map for each radiation beam based on the one or more constraints provided by the reference treatment plan. The fluence map indicates how intense each beam should be at each point of the MLC aperture. The fluence map is also referred to as an intensity profile, and is represented by a two-dimensional, nonnegative function $I_a(x,y)$ for $a=1, 2, 3, \ldots, k$, where k is the number of beam angles in use. The fluence maps can be determined using a fluence map optimization algorithm based on the constraints provided by the reference treatment plan and the segment information determined from the SAM algorithm. Any suitable fluence map optimization algorithm can be used to generate the fluence maps.

Figure 7:
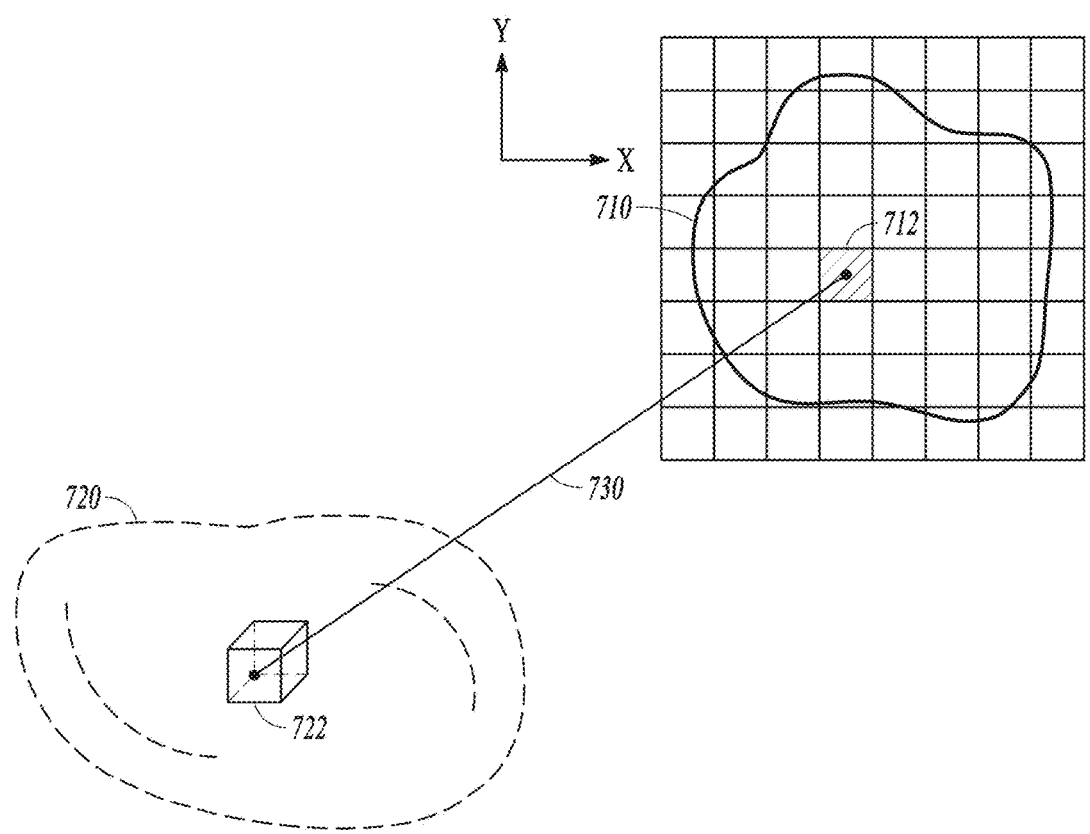
FIG. 7 illustrates an exemplary method of determining dose distribution, according to some embodiments of the present disclosure.

In step 460, control console 110 may determine a dose distribution based on the fluence maps. FIG. 7 shows an exemplary MLC aperture 710 and an exemplary anatomical region of interest 720. An exemplary algorithm for calculating the dose distribution will be described in connection with FIG. 7. The algorithm starts by discretizing the MLC aperture 710 for each beam angle by putting a rectangular grid $\{(x_i,y_i)\}$ on it. The actual number of these small rectangular elements, or "bixels" (such as 712), depends not only on physical sizes of the MLC device (such as the width of the MLC leaves), but also on the beam angles and the geometry of the anatomical region of interest 720. For example, if a beam emitting from a given grid point is determined not to have a significant intersection with or impact on anatomical region of interest 720, then this particular grid point will be omitted from consideration. With this discretization, each MLC aperture is broken into hundreds (or even thousands) of discrete "bixels" and, correspondingly, each radiation beam is broken into as many discrete "beamlets" (e.g., 730).

In addition, anatomical region of interest 720 also needs to be discretized. Region 720 is a 3D volume containing the target to be treated as well as OARs surrounding the target. Region 720 can be discretized into small 3D rectangular elements (such as 722) known as "voxels." With this discretization, the dose received by a voxel vi is the summation of all beamlet intensity values respectively multiplied by a contribution coefficient, indicating the amount of dose received by the i-th voxel per unit intensity emission from that beamlet. All the contribution coefficients can be arranged in a matrix form known as the influence matrix or kernel matrix. Once the influence matrix is determined, the dose distribution can be determined based on the fluence maps. The influence matrix can be determined by various methods. For example, Monte Carlo sampling technique can be used.

In step 470, control console 110 may determine a beam modulation property of a new treatment plan based on the dose distribution and the segment information (e.g., determined using the SAM algorithm). For example, control console 110 may start a warm-start optimization using the dose distribution determined in step 460 as the goal dose distribution instead of the dose constraints provided by the reference plan. Instead of evaluating the dose-volume histograms resulting from a set of plan parameters against the dose constraints (which does not necessarily correspond to any particular dose distribution), control console 110 may use the dose distribution determined based on the fluence maps as the goal distribution, which has a more direct connection with beam modulation properties such as MLC aperture shapes and weighting factors. In addition, the warm-start optimization may start from the segment information (e.g., aperture shapes resulting from the SAM algorithm) determined in step 440. Compared to the traditional leaf sequencing method in which a fluence map is constructed from arbitrary aperture shapes (some may not even be achievable by the particular MLC used in the treatment), the readily achievable aperture shapes may improve the speed of the optimization. The optimization result may include one or more beam modulation properties such as a set of optimized MLC aperture shapes to be used in the new treatment plan. The one or more beam modulation properties may also include weighting factors respectively associated with the optimized MLC apertures. For example, the weighting factors may be respectively associated with the segments (each having a corresponding aperture shape) and indicate the proportions of radiation does to be delivered through the corresponding segments.

Figure 8:
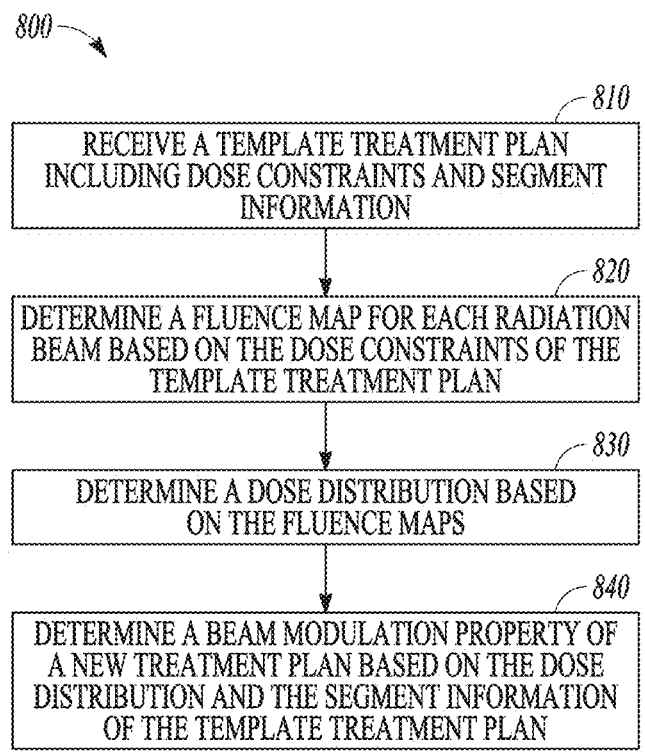
FIG. 8 is a flowchart of an exemplary method of creating a new radiation treatment plan for a new patient, according to some embodiments of the present disclosure.

FIG. 8 is a flow chart of an exemplary method 800 for creating a new treatment plan for a new patient based on a template treatment plan. Referring to FIG. 8, method 800 is similar to method 400 except that the reference treatment plan in method 800 is a template treatment plan and that no SAM is performed because there is no prior treatment plan or prior medical image to compare with. In step 810, control console 110 may receive a template treatment plan including dose constraints and segment information. The template treatment plan may be provided as a sample and may be tailored to particular situations of individual patients. The template treatment plan may be stored in database 120. In step 820, control console 110 may determine a fluence map for each radiation beam based on the dose constraints of the template treatment plan, similar to step 450. In step 830, control console 110 may determine a dose distribution based on the fluence maps, similar to step 460. In step 840, control console 110 may determine at least one beam modulation property of the new treatment plan based on the dose distribution and the segment information of the template treatment plan, similar to step 470. Using the dose distribution determined based on the fluence maps as the goal dose may improve the speed of the planning process compared with using the dose constraints. In addition, the warm-start optimization starts with aperture shapes that are readily achievable, thereby reducing the processing time of the optimization.

Figure 9:
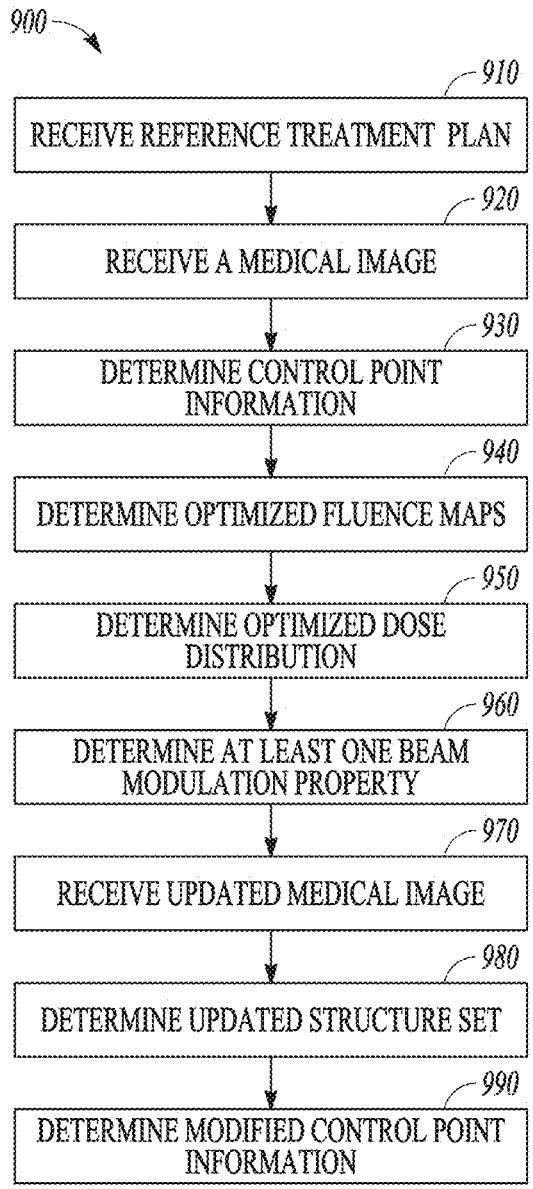
FIG. 9 is a flowchart of an exemplary method for creating a treatment plan for a patient based on a reference treatment plan.

FIG. 9 is a flow chart of an exemplary method 900 for creating a treatment plan for a patient based on a reference treatment plan. In step 910, control console 110 may receive a reference treatment plan including one or more dose constraints and control point information. The reference treatment plan may be stored in database 120. In step 920, control console 110 may receive at least one medical image and a structure set not included with the reference treatment plan, either from medical imaging device 140 or from database 120. A new treatment plan can then be determined based on the received at least one medical image and structure set. The new treatment plan can be for the same patient for which the reference plan was performed. The new treatment plan can be for a different patient than for which the reference plan was performed. In step 930, control point information of a plurality of radiation beams can be determined by the control console 110 based on the reference treatment plan and the plurality of radiation beams can be registered to the received at least one medical image. In step 940, an optimized fluence map can be determined by the control console 110 for each of the plurality of radiation beams. Each optimized fluence map can be determined based on the one or more dose constraints included in the reference treatment plan using a fluence map optimization algorithm and the received at least one medical image and structure set. In step 950, an optimized dose distribution can be determined by the control console based on the optimized fluence maps of the plurality of radiation beams. In step 960, at least one beam modulation property of the new treatment plan can be determined by the control console using a warm-start optimization algorithm based on the control point information included in the reference treatment plan by optimizing shapes and/or weights of the control points and/or weights of the plurality of radiation beams to achieve the optimized dose distribution. In some embodiments, the method 900 can also include steps 970-990. In step 970, an updated medical image can be received by the control console 110. In step 980, an updated structure set for the updated medical image can be determined by the control console 110. In some embodiments, the updated structure set can be received by the control console 110. A difference between the updated structure set and the structure set included with the reference treatment plan can be determined by the control console 110. In step 990, modified control point information based on the difference can be determined by the control console by using a segment aperture morphing (SAM) algorithm. The modified control point information can be used for the warm start optimization.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules. Embodiments may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A radiotherapy treatment planning system, comprising:
    a memory device storing computer-executable instructions; and
    at least one processor device communicatively coupled to the memory device, wherein the computer-executable instructions, when executed by the at least one processor device, cause the processor device to perform operations including:
        receiving a reference treatment plan, the reference treatment plan including one or more dose constraints and control point information;
        receiving at least one medical image and a structure set not included with the received reference treatment plan;
        determining a new treatment plan based on the received at least one medical image and structure set;
        determining, based on the reference treatment plan, control point information of a plurality of radiation beams and registering the plurality of radiation beams to the received at least one medical image;
        determining an optimized fluence map for each of the plurality of radiation beams based on the one or more dose constraints included in the reference treatment plan, using a fluence map optimization algorithm and the received at least one medical image and structure set;
        determining an optimized dose distribution based on the optimized fluence maps of the plurality of radiation beams; and
        determining at least one beam modulation property of the new treatment plan using a warm-start optimization algorithm based on the control point information included in the reference treatment plan by optimizing shapes and/or weights of the control points and/or weights of the plurality of radiation beams to achieve the optimized dose distribution.

2. The radiotherapy treatment planning system of claim 1, wherein the new treatment plan is for the same patient for which the reference plan was performed.

3. The radiotherapy treatment planning system of claim 1, wherein the new treatment plan is for a different patient than for which the reference plan was performed.

4. The radiotherapy treatment planning system of claim 1, wherein the operations further include:
    receiving at least one updated medical image;
    determining an updated structure set for the updated medical image or receiving an updated structure set;
    determining a difference between the updated structure set and a structure set included with the reference treatment plan; and
    determining modified control point information based on the difference using a segment aperture morphing algorithm and using the modified control point information for the warm start optimization.

5. The radiotherapy treatment planning system of claim 4, wherein receiving an updated medical image includes receiving an updated medical image from the same patient for which the reference plan was performed.

6. The radiotherapy treatment planning system of claim 4, wherein receiving an updated medical image includes receiving an updated medical image for a different patient than for which the reference plan was performed.

7. The radiotherapy treatment planning system of claim 1, wherein the reference treatment plan is based on a predetermined plan template and the new treatment plan is for a different patient than for which the reference plan was performed.

8. The radiotherapy treatment planning system of claim 1, wherein the control point information includes shapes of a set of multileaf collimator apertures through which the plurality radiation beams are modulated.

9. The radiotherapy treatment planning system of claim 1, wherein the one or more dose constraints include a limitation on radiation dosage received by one or more organs at risk (OARs).

10. The radiotherapy treatment planning system of claim 1, wherein the at least one beam modulation property of the new treatment plan includes shapes of a set of optimized multileaf collimator apertures through which the plurality of radiation beams are modulated.

11. The radiotherapy treatment planning system of claim 10, wherein the at least one beam modulation property of the new treatment plan includes weighting factors respectively associated with the optimized multileaf collimator apertures in the set, the weighting factors indicating relative proportions of radiation doses to be delivered through the respective optimized multileaf collimator apertures.

12. A method, implemented by at least one processor device executing computer-executable instructions, for performing radiotherapy treatment planning, the method comprising:
receiving a reference treatment plan, the reference treatment plan including one or more dose constraints and control point information;
receiving at least one medical image and a structure set not included with the received reference treatment plan;
determining a new treatment plan based on the received at least one medical image and structure set;
determining, based on the reference treatment plan, control point information of a plurality of radiation beams and registering the plurality of radiation beams to the received at least one medical image;
determining an optimized fluence map for each of the plurality of radiation beams based on the one or more dose constraints included in the reference treatment plan, using a fluence map optimization algorithm and the received at least one medical image and structure set;
determining an optimized dose distribution based on the optimized fluence maps of the plurality of radiation beams; and
determining at least one beam modulation property of the new treatment plan using a warm-start optimization algorithm based on the control point information included in the reference treatment plan by optimizing shapes and/or weights of the control points and/or weights of the plurality of radiation beams to achieve the optimized dose distribution.

13. The method of claim 12, wherein the new treatment plan is for the same patient for which the reference plan was performed.

14. The method of claim 12, wherein the new treatment plan is for a different patient than for which the reference plan was performed.

15. The method of claim 12, comprising:
receiving at least one updated medical image;
determining an updated structure set for the updated medical image or receiving an updated structure set;
determining a difference between the updated structure set and a structure set included with the reference treatment plan; and
determining modified control point information based on the difference using a segment aperture morphing algorithm and using the modified control point information for the warm start optimization.

16. The method of claim 15, wherein receiving an updated medical image includes receiving an updated medical image from the same patient for which the reference plan was performed.

17. The method of claim 15, wherein receiving an updated medical image includes receiving an updated medical image for a different patient than for which the reference plan was performed.

18. The method of claim 15, wherein the reference treatment plan is based on a predetermined template and the new treatment plan is for a different patient than for which the reference plan was performed.

19. The method of claim 12, wherein the control point information includes shapes of a set of multileaf collimator apertures through which the plurality of radiation beams are modulated.

20. The method of claim 12, wherein the one or more dose constraints include a limitation on radiation dosage received by one or more organs at risk (OARs).

21. The method of claim 12, wherein the at least one beam modulation property of the new treatment plan includes shapes of a set of optimized multileaf collimator apertures through which the plurality of radiation beams are modulated.

22. The method of claim 21, wherein the at least one beam modulation property of the new treatment plan includes weighting factors respectively associated with the optimized multileaf collimator apertures in the set, the weighting factors indicating relative proportions of radiation doses to be delivered through the respective optimized multileaf collimator apertures.

23. A non-transitory computer-readable medium that stores a set of instructions that is executable by at least one processor of a device to cause the device to perform a method for radiotherapy treatment planning, the method comprising:
receiving a reference treatment plan, the reference treatment plan including one or more dose constraints and control point information;
receiving at least one medical image and a structure set not included with the received reference treatment plan;
determining a new treatment plan based on the received at least one medical image and structure set;
determining, based on the reference treatment plan, control point information of a plurality of radiation beams and registering the plurality of radiation beams to the received at least one medical image;
determining an optimized fluence map for each of the plurality of radiation beams based on the one or more dose constraints included in the reference treatment plan, using a fluence map optimization algorithm and the received at least one medical image and structure set;
determining an optimized dose distribution based on the optimized fluence maps of the plurality of radiation beams; and
determining at least one beam modulation property of the new treatment plan using a warm-start optimization algorithm based on the control point information included in the reference treatment plan by optimizing shapes and/or weights of the control points and/or weights of the plurality of radiation beams to achieve the optimized dose distribution.

24. The computer-readable medium of claim 23, wherein the new treatment plan is for the same patient for which the reference plan was performed.

25. The computer-readable medium of claim 23, wherein the new treatment plan is for a different patient than for which the reference plan was performed.

26. The computer-readable medium of claim 23, wherein the set of instructions that is executable by the at least one processor of the device cause the device to further perform:
   receiving at least one updated medical image;
   determining an updated structure set for the updated medical image or receiving an updated structure set;
   determining a difference between the updated structure set and a structure set included with the reference treatment plan; and
   determining modified control point information based on the difference using a segment aperture morphing algorithm and using the modified control point information for the warm start optimization.

27. The computer-readable medium of claim 26 wherein receiving an updated medical image includes receiving an updated medical image from the same patient for which the reference plan was performed.

28. The computer-readable medium of claim 26 wherein receiving an updated medical image includes receiving an updated medical image for a different patient than for which the reference plan was performed.

* * * * *